United States Patent
Ueda

[11] Patent Number: 5,897,488
[45] Date of Patent: Apr. 27, 1999

[54] BENDING INSERTION INSTRUMENT TO BE INSERTED INTO A BODY CAVITY THROUGH AN ENDOSCOPE

[75] Inventor: Yasuhiro Ueda, Tokyo, Japan

[73] Assignee: Olympus Optical Co., Ltd., Tokyo, Japan

[21] Appl. No.: 08/601,701

[22] Filed: Feb. 15, 1996

Related U.S. Application Data

[62] Division of application No. 08/303,894, Sep. 9, 1994, abandoned, which is a continuation of application No. 07/940,186, Sep. 3, 1992, abandoned.

[30] Foreign Application Priority Data

Sep. 17, 1991 [JP] Japan ..................................... 3-236239
Jul. 1, 1992 [JP] Japan ..................................... 4-174465

[51] Int. Cl.$^6$ ............................................. A61B 1/005
[52] U.S. Cl. ........................................... 600/143; 600/151
[58] Field of Search ................................. 600/151, 153, 600/143, 113, 114; 604/280, 95

[56] References Cited

U.S. PATENT DOCUMENTS

| | | | |
|---|---|---|---|
| 4,290,421 | 9/1981 | Siegmund | 128/6 |
| 4,726,355 | 2/1988 | Okada | 128/4 |
| 4,742,817 | 5/1988 | Kawashima et al. | 600/151 |
| 4,794,912 | 1/1989 | Lia . | |
| 4,832,473 | 5/1989 | Ueda . | |
| 4,846,573 | 7/1989 | Taylor et al. | 128/4 |
| 4,870,951 | 10/1989 | Suzuki . | |
| 4,890,602 | 1/1990 | Hake . | |
| 4,962,751 | 10/1990 | Krauter . | |
| 4,977,886 | 12/1990 | Takehana et al. | 128/4 |
| 5,014,515 | 5/1991 | Krauter . | |
| 5,018,506 | 5/1991 | Danna et al. . | |
| 5,048,956 | 9/1991 | Sakamoto et al. . | |
| 5,196,928 | 3/1993 | Karasawa et al. | 600/13 |
| 5,531,664 | 7/1996 | Adachi et al. | 600/149 |

FOREIGN PATENT DOCUMENTS

| | | | |
|---|---|---|---|
| 0199870 | 11/1986 | European Pat. Off. . | |
| 59-2344 | 1/1984 | Japan . | |
| 59-48710 | 3/1984 | Japan . | |
| 1110241 | 4/1989 | Japan . | |
| 3-86143 | 4/1991 | Japan . | |
| 3-97426 | 4/1991 | Japan . | |
| 3-173371 | 7/1991 | Japan . | |
| 1153334 | 5/1969 | United Kingdom . | |
| 8704080 | 7/1987 | WIPO | 604/280 |
| 8902762 | 4/1989 | WIPO | 604/280 |

*Primary Examiner*—John P. Leubecker
*Attorney, Agent, or Firm*—Frishauf, Holtz, Goodman, Langer & Chick

[57] ABSTRACT

An endoscope apparatus includes an endoscope having a distal end, a port at the distal end, and a channel extending through the endoscope to the distal end and communicating with the port; and a bending insertion instrument extensible through the channel and the port. The bending insertion instrument includes angle wires provided at a distal end portion of the bending insertion instrument, and shape memory alloy wires connected to proximal end portions of the angle wires, the angle wires having a lower electrical resistance than an electrical resistance of the shape memory alloy wires. The bending insertion instrument is inserted through the channel of the endoscope such that a portion of the bending insertion instrument, which includes the shape memory alloy wires is located in the channel of the endoscope, and a bending portion of the bending insertion instrument which includes the angle wire is located at the distal end portion of the bending insertion instrument and is projected through the port of the endoscope.

35 Claims, 25 Drawing Sheets

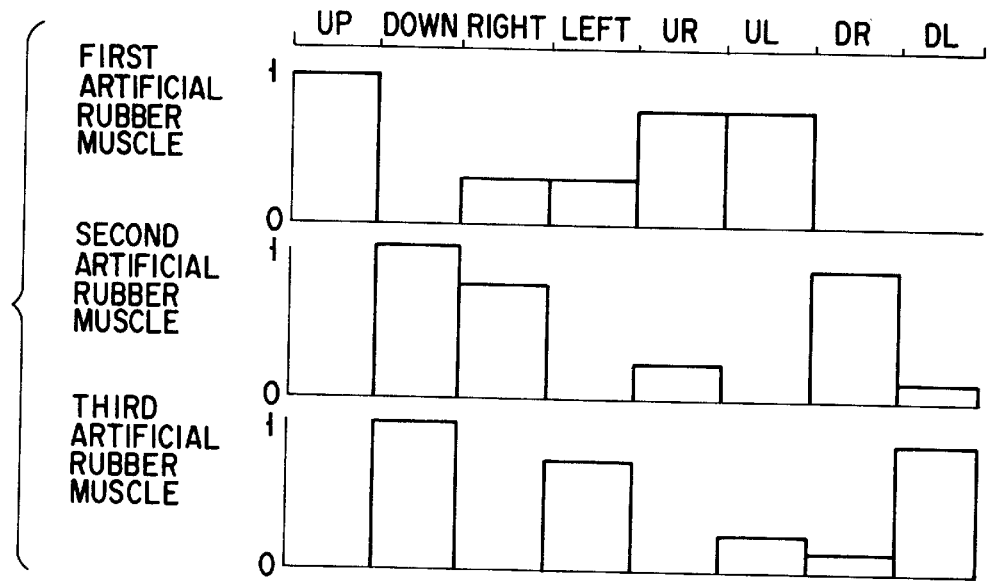
F I G. 4
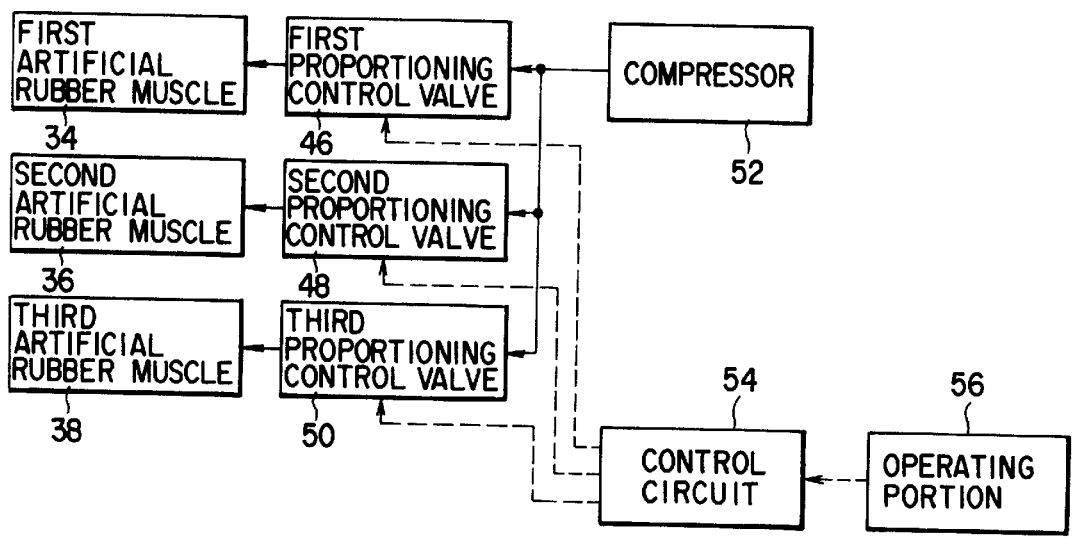
F I G. 5

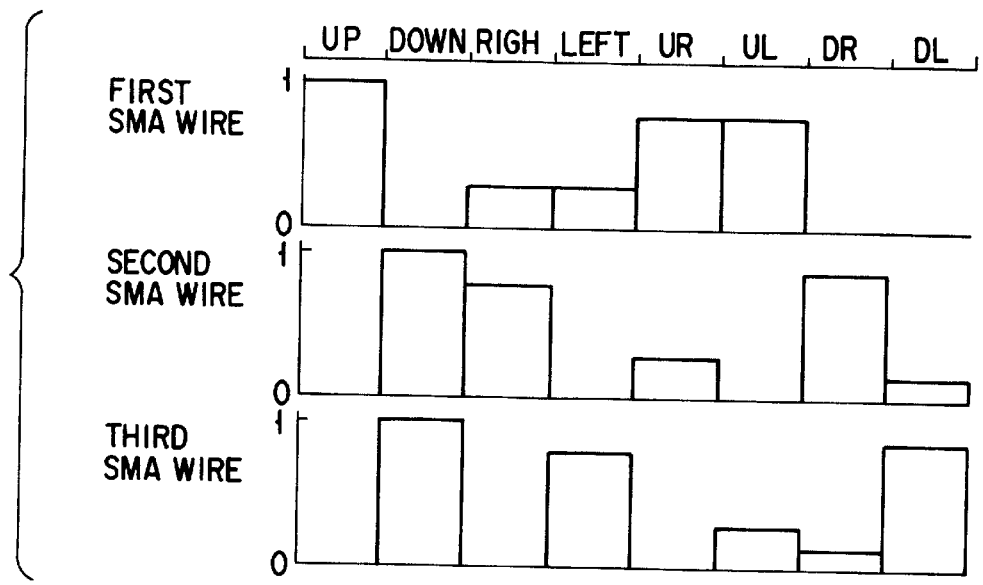
F I G. 7
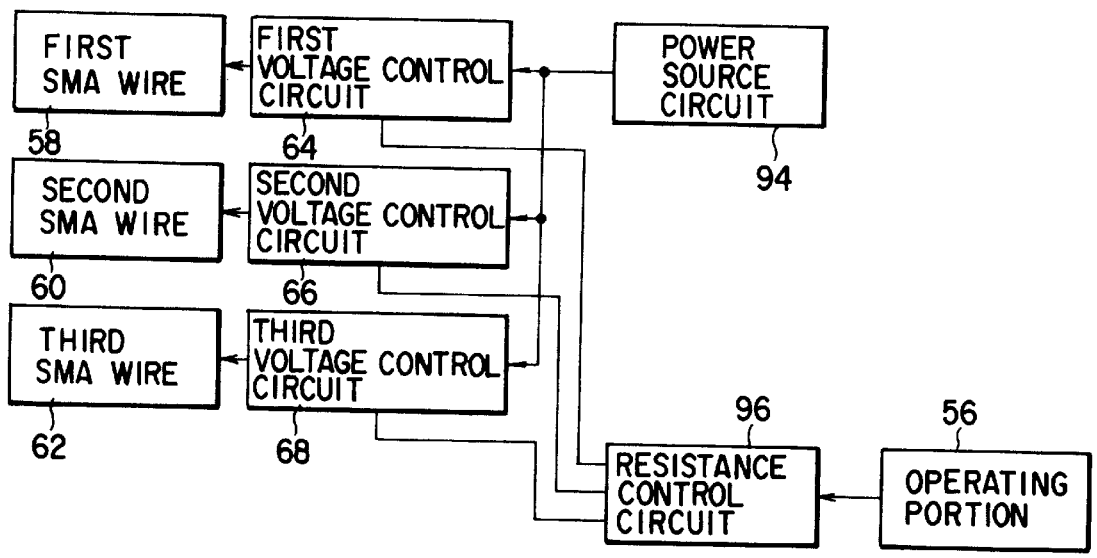
F I G. 8A

FIG. 11(a)
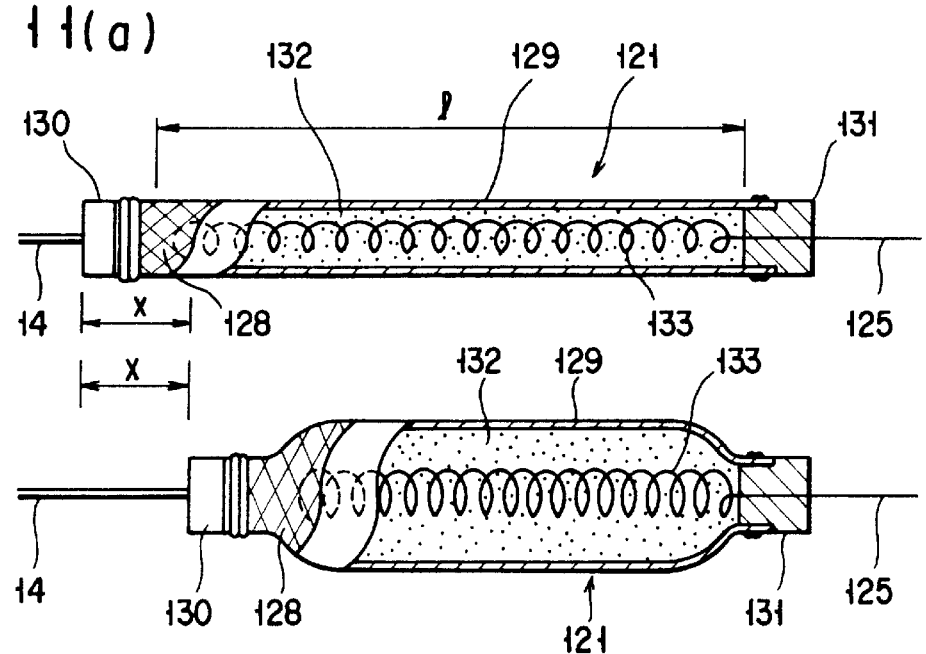
FIG. 11(b)
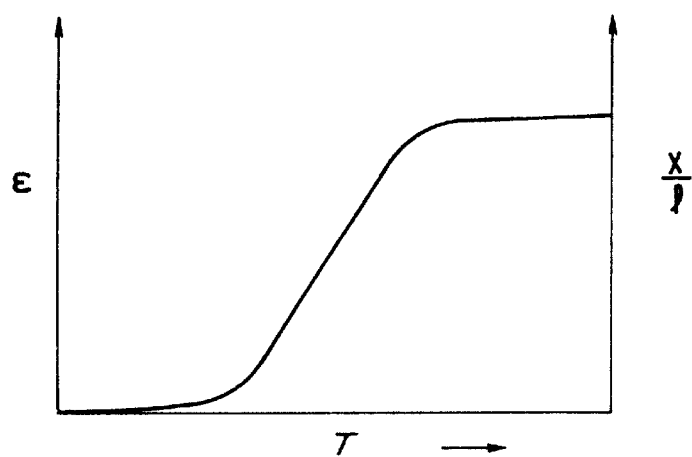
FIG. 12

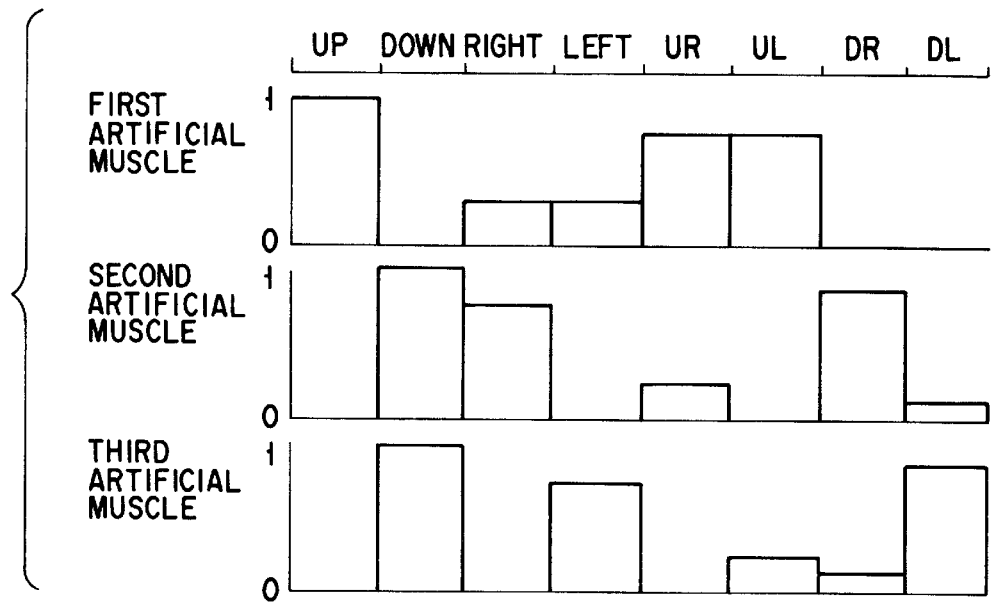
F I G. 13
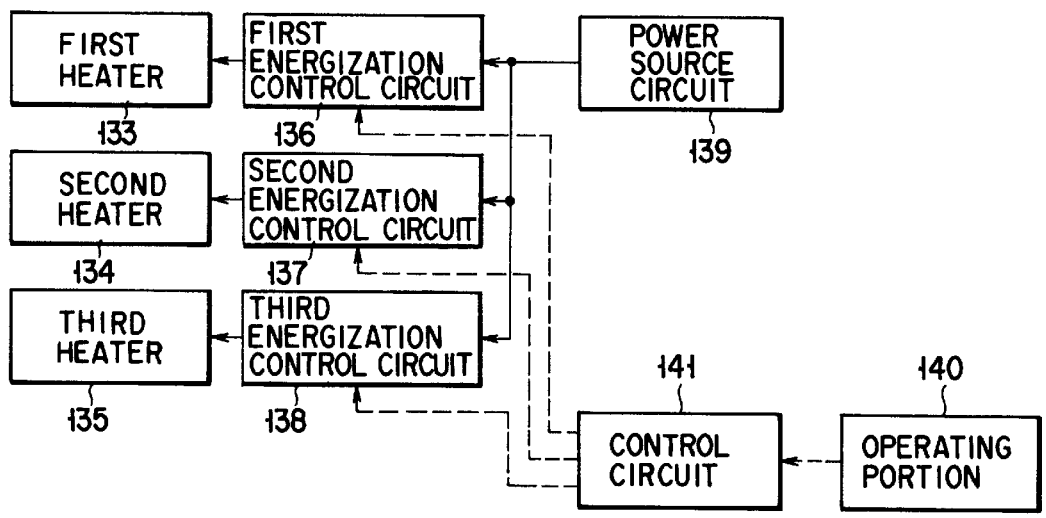
F I G. 14

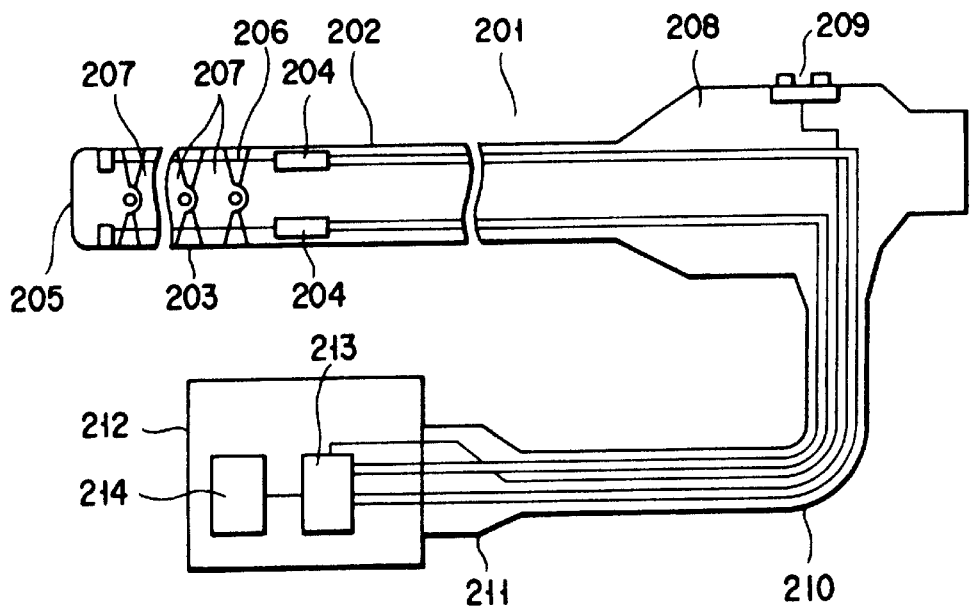
F I G. 15
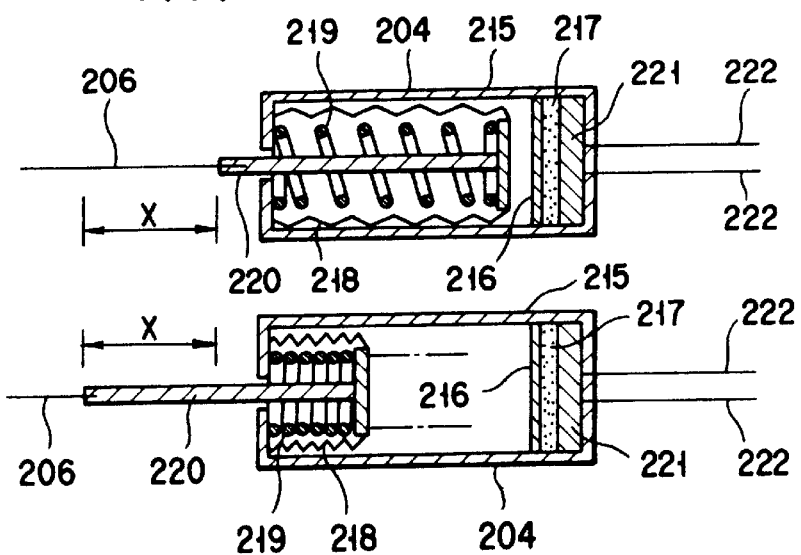
F I G. 16(b)

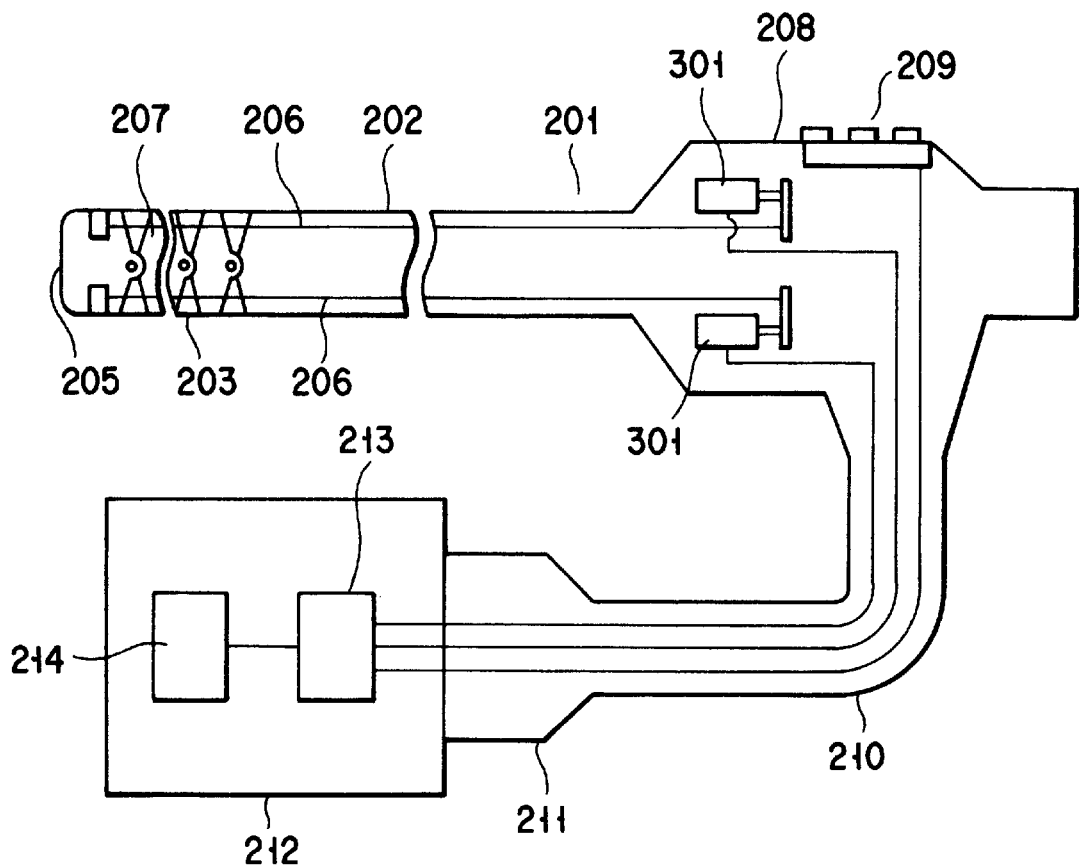
F I G. 18
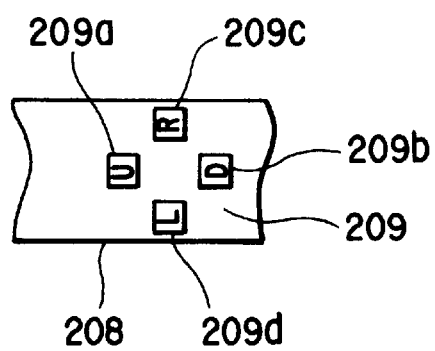
F I G. 19

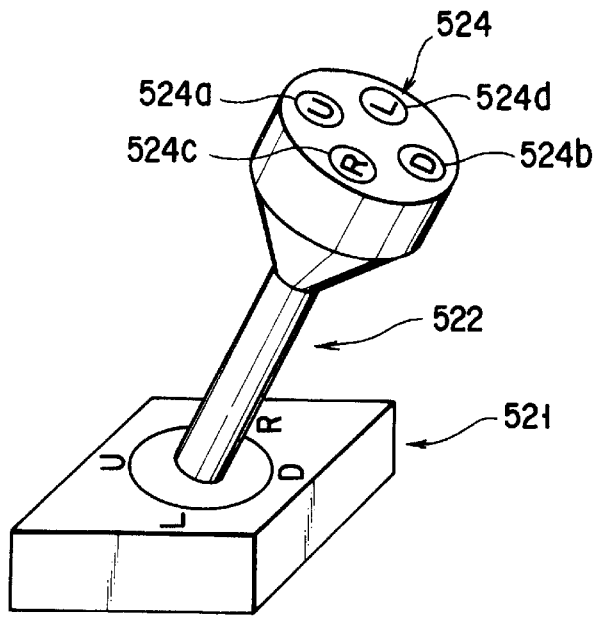
F I G. 27
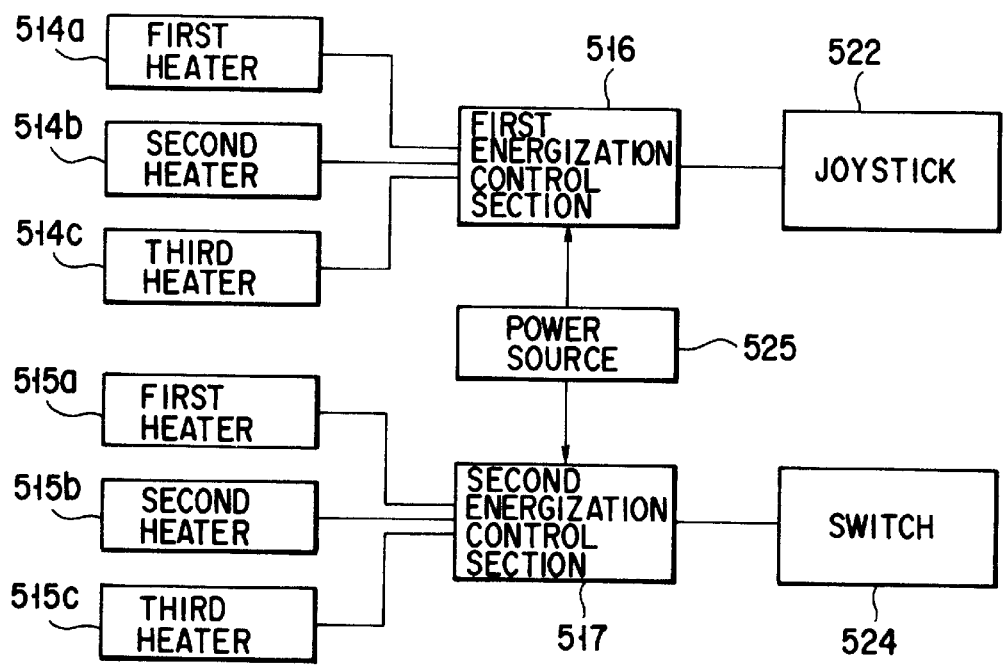
F I G. 28

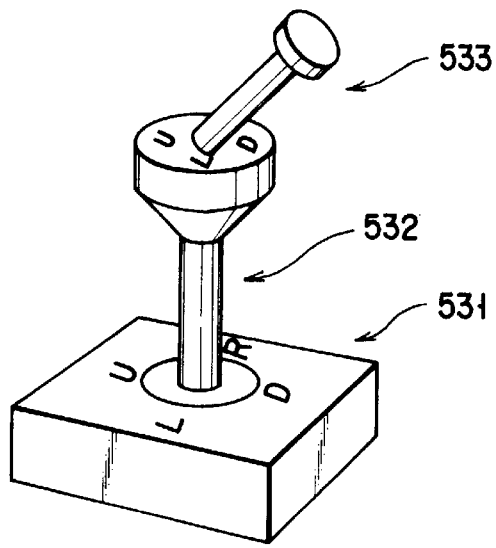
F I G. 29
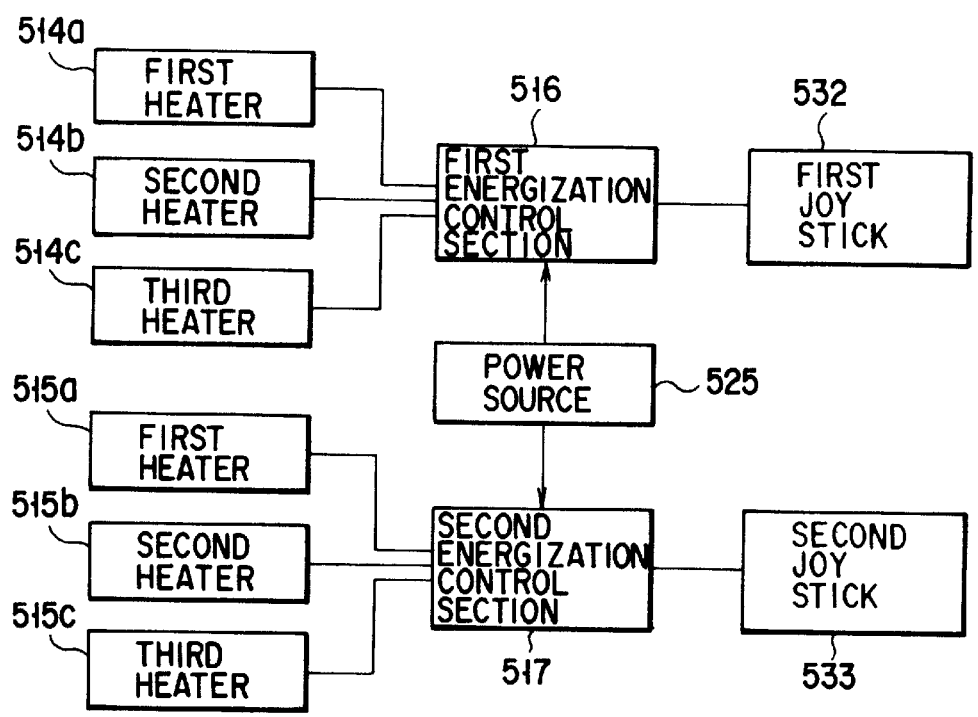
F I G. 30

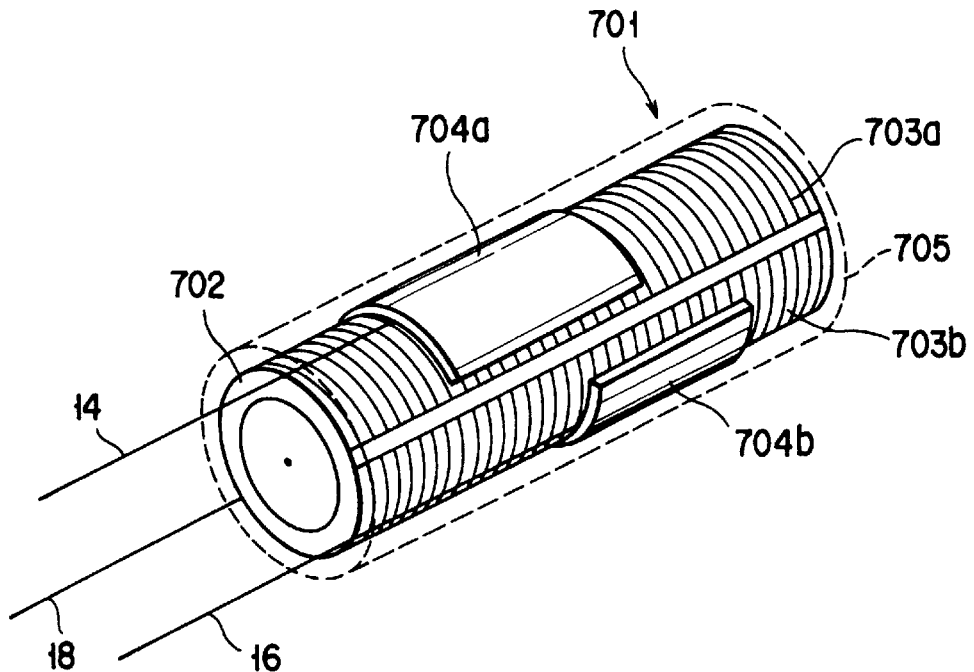
F I G. 32
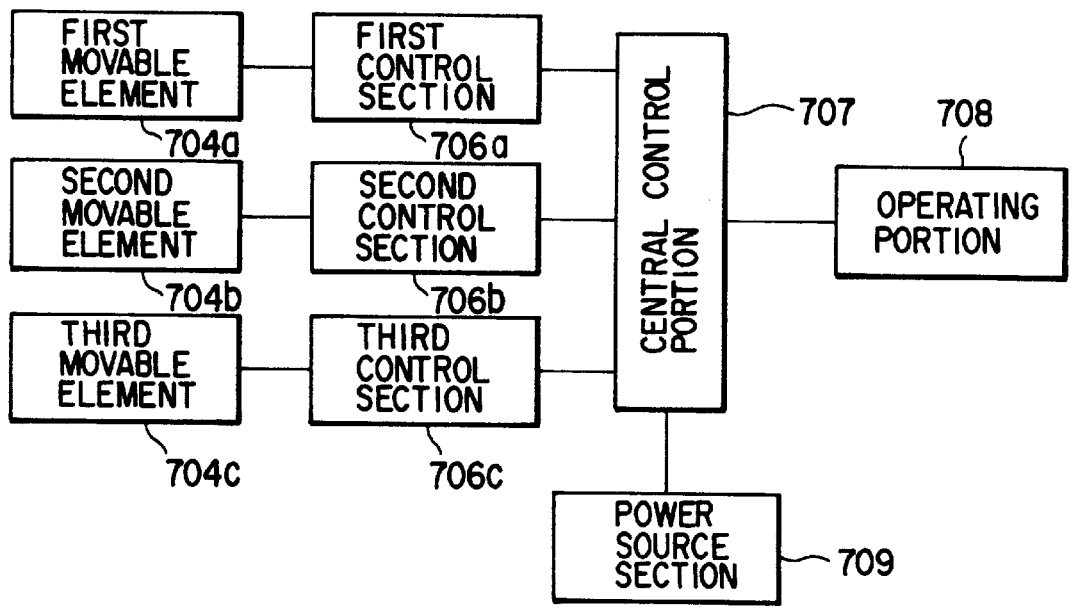
F I G. 33

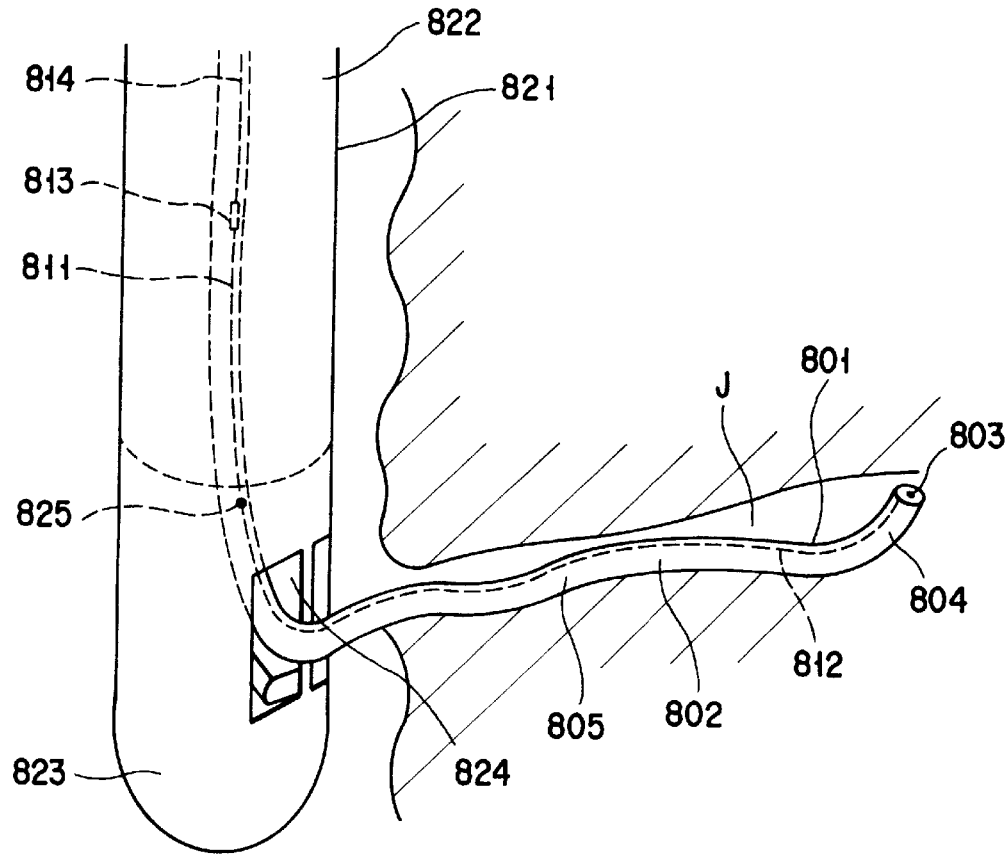
F I G. 34
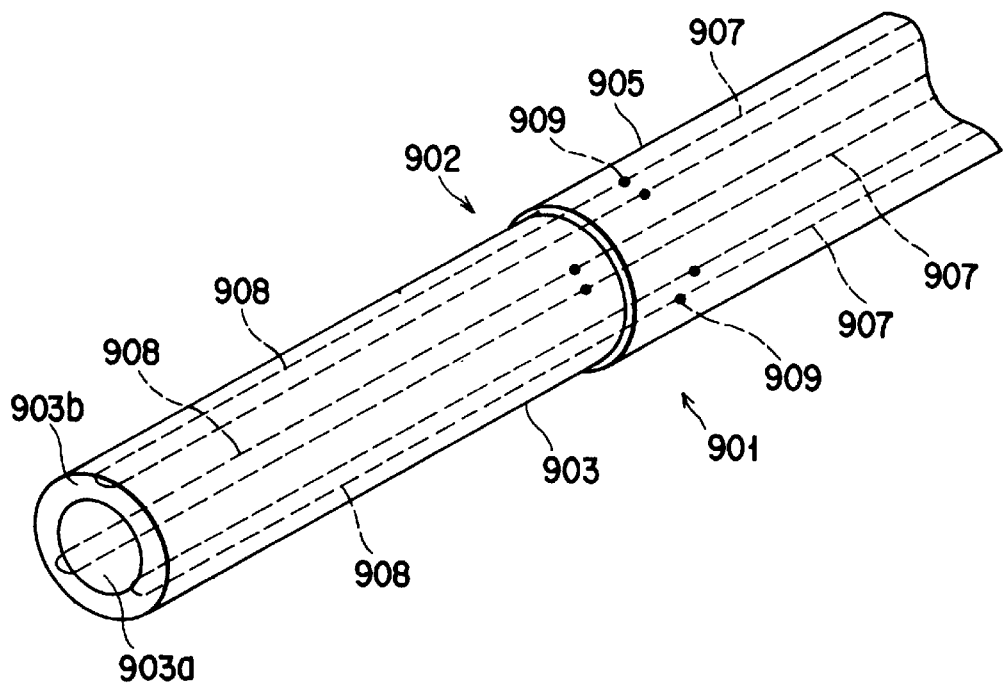
F I G. 35

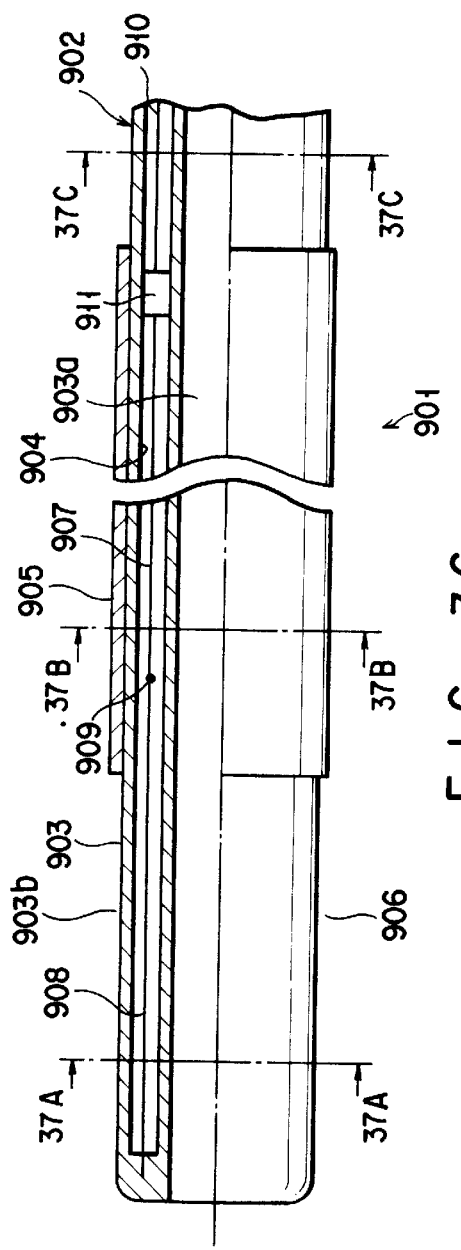
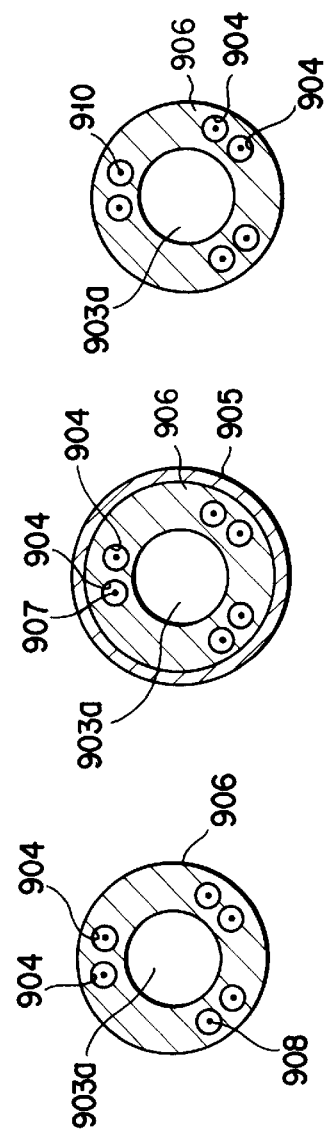
FIG. 36
FIG. 37A   FIG. 37B   FIG. 37C

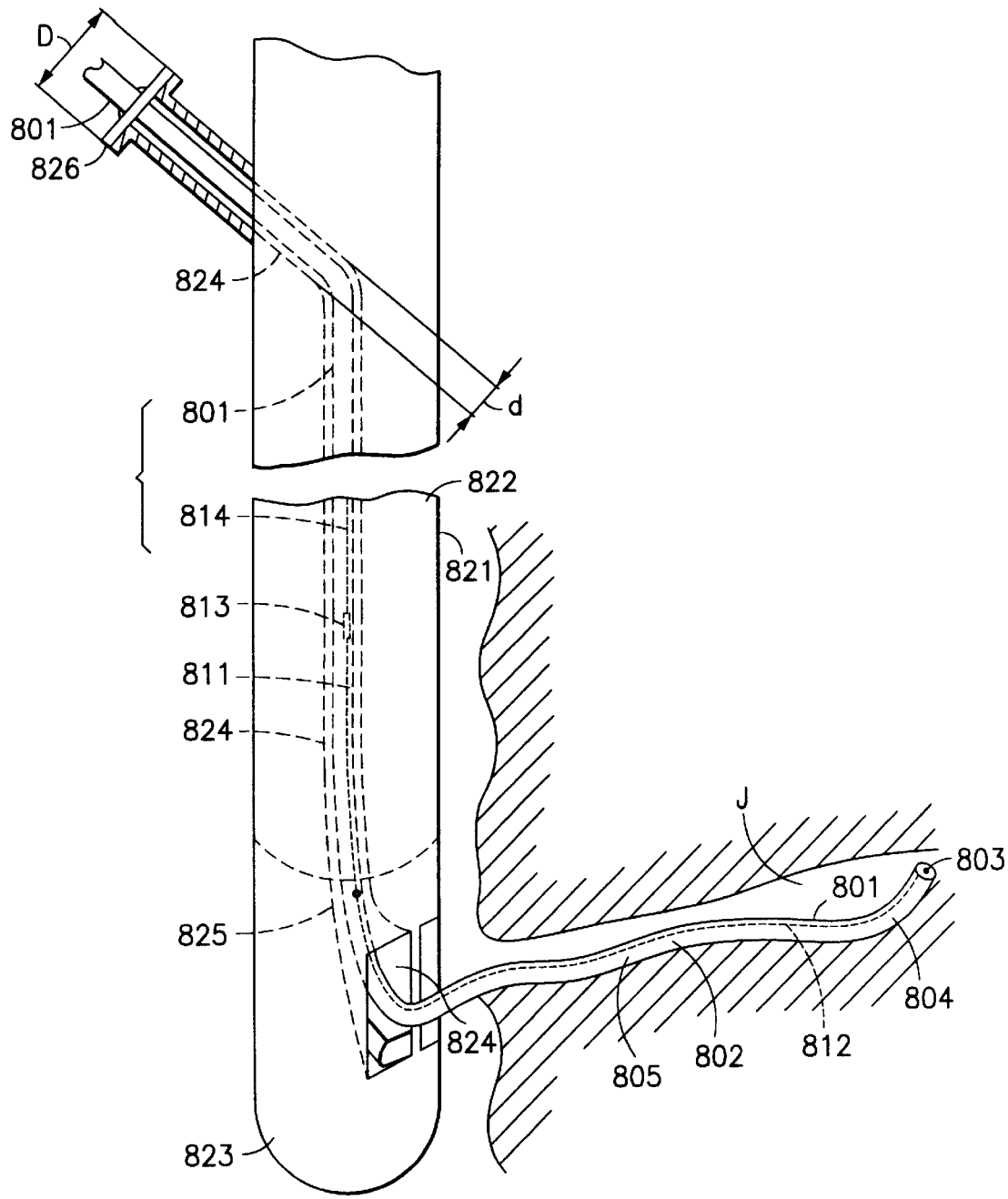
F I G. 40

BENDING INSERTION INSTRUMENT TO BE INSERTED INTO A BODY CAVITY THROUGH AN ENDOSCOPE

This application is a Division of application Ser. No. 08/303,894, filed Sep. 9, 1994, (now abandoned) which is a Continuation of application Ser. No. 07/940,186, filed Sep. 3, 1992 (now abandoned).

BACKGROUND OF THE INVENTION

1. Field of the Invention

The present invention relates to a bending operation apparatus for a tubular insertion member, which is designed to bend the insertion portion of, e.g., an endoscope, or a tubular insertion member such as a catheter in arbitrary directions.

2. Description of the Related Art

In a conventional bending operation apparatus, a bending portion, which can be bent/deformed, is formed at the insertion portion of, e.g., an endoscope or at the distal end side of a flexible tube such as a catheter. The apparatus allows an operator to remotely control a bending operation of the bending portion through an operating portion at hand.

A bending operation apparatus of this type has been developed, which is designed such that small actuators constituted by shape memory alloy (SMA) members, pneumatic type artificial rubber muscles, and the like are arranged at the insertion portion of an endoscope, i.e., the distal end side of a flexible tube, and a bending operation of the bending portion is performed by the small actuators through angle wires.

In this case, a plurality of bending pieces are arranged in the bending portion along its axial direction and are pivotally coupled to each other. One end of each angle wire is fixed to the distal end of the bending portion. Each of the above-mentioned small actuators is fixed to the other end of a corresponding one of the angle wires.

When the small actuators are operated, two or four angle wires are pulled, thus freely bending the bending portion in two or four directions through the respective bending pieces.

If the apparatus is designed such that four angle wires are independently pulled to allow bending operations in four directions, the bending portion of the endoscope can be aimed in an arbitrary direction within a range of 360× by combining bending operations performed through a plurality of angle wires.

In the conventional bending operation apparatus having the above-described arrangement, however, small actuators, equal in number to the bending directions of the bending portion, must be independently arranged at the distal end side of the flexible tube. For example, if four angle wires are used to bend the bending portion in four directions, four small actuators need to be independently arranged at the distal end side of the flexible tube. This interferes with a reduction in the diameter of the flexible tube.

SUMMARY OF THE INVENTION

The present invention has been made in consideration of the above situation, and has as its object to provide a bending operation apparatus for a tubular insertion member, which allows simplification of the internal arrangement of the insertion portion of a tubular insertion member to achieve a reduction in the diameter of a flexible tube.

In order to achieve the above object, according to the present invention, there is provided a bending operation apparatus for a tubular insertion member, which has a bending portion, which can be bent/deformed, on a distal end of a tubular insertion portion to be inserted into a digestive organ, a body cavity, an industrial tube, or a working space, the insertion portion having a proximal end coupled to an operating portion at hand, i.e., on a manual operation side which serves to remotely control a bending operation of the bending portion, comprising:

three angle wires, arranged in the bending portion, for performing a bending operation;

three actuators for independently operating the three angle wires; and control means for arbitrarily controlling operating amounts of the three angle wires through the three actuators.

According to the present invention, therefore, the operating amounts of the three angle wires are controlled by the control means, and the angle wires are operated through the actuators, thus bending the bending portion in a predetermined direction.

Since the number of actuators in the present invention is smaller than that in the prior art, the assembly performance of the mechanism can be improved, and a reduction in the diameter of the flexible tube can be achieved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a chart showing pressurized states of first to third artificial rubber muscles during a bending operation of a bending portion in the first embodiment;

FIG. 5 is a block diagram showing a driving circuit for the bending mechanism of the flexible tube;

FIG. 7 is a chart showing states of voltages applied to first to third SMA wires during a bending operation of a bending portion in the second embodiment;

FIG. 8A is a block diagram showing a driving circuit for the bending mechanism of the flexible tube;

FIGS. 11(a) and 11(b) are views for explaining an operation of an artificial rubber muscle according to the third embodiment;

FIG. 12 is a graph showing the relationship between a heating temperature T, $\epsilon$, and x/l;

FIG. 13 is a chart showing pressurized states of first to third artificial rubber muscles during a bending operation of a bending portion;

FIG. 14 is a block diagram showing a driving circuit for the bending mechanism;

FIG. 15 is a schematic view showing the arrangement of the bending mechanism of a flexible tube according to the fourth embodiment of the present invention;

FIGS. 16(a) and 16(b) are views for explaining an operation of an actuator according to the fourth embodiment;

FIG. 18 is a schematic view showing the arrangement of the bending mechanism of a flexible tube according to the sixth embodiment of the present invention;

FIG. 19 is a plan view showing the bending switch of an operating portion;

FIG. 27 is a perspective view showing a controller according to the ninth embodiment of the present invention;

FIG. 28 is a block diagram showing a driving circuit according to the ninth embodiment;

FIG. 29 is a perspective view showing a controller according to the tenth embodiment of the present invention;

FIG. 30 is a block diagram showing a driving circuit according to the tenth embodiment;

FIG. 32 is a perspective view showing a schematic arrangement of an actuator according to twelfth embodiment of the present invention;

FIG. 33 is a block diagram showing a driving circuit for each actuator according to the twelfth embodiment;

FIG. 34 is a schematic view showing the arrangement of the thirteenth embodiment of the present invention;

FIG. 35 is a perspective view showing a schematic arrangement of the fourteenth embodiment of the present invention;

FIG. 36 is a partially cutaway side view showing a main portion of a catheter according to the fourteenth embodiment;

FIG. 37A is a sectional view taken along a line 37A—37A in FIG. 36;

FIG. 37B is a sectional view taken along a line 37B—37B in FIG. 36;

FIG. 37C is a sectional view taken along a line 37C—37C in FIG. 36;

FIG. 40 is a schematic view similar to FIG. 34, and showing a stopper.

DETAILED DESCRIPTION OF THE PREFERRED EMBODIMENTS

Figure 1:
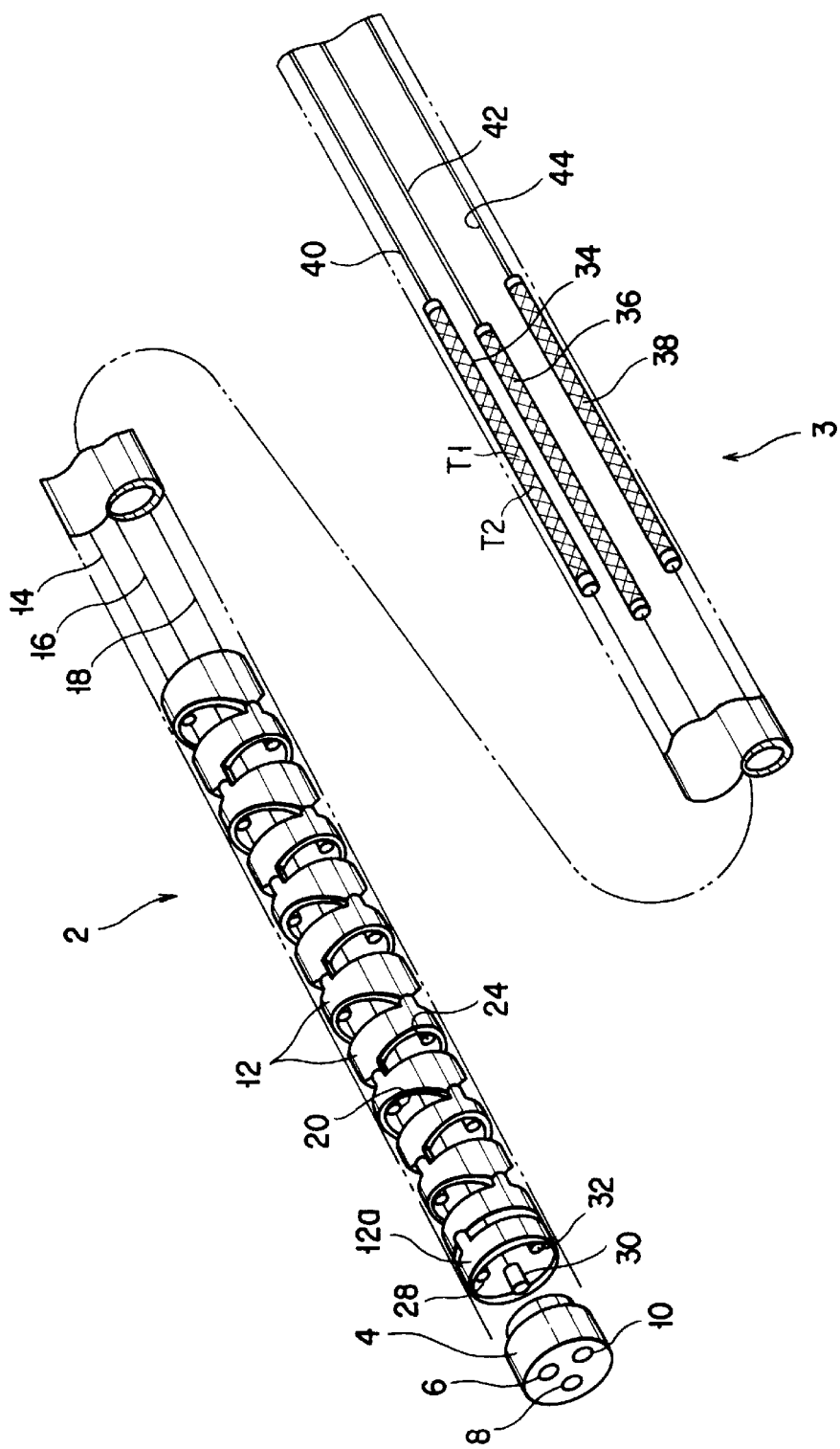
FIG. 1 is a perspective view schematically showing the arrangement of the bending mechanism of a flexible tube according to the first embodiment of the present invention.

A bending operation apparatus for a tubular insertion member according to the first embodiment of the present invention will be described below with reference to FIGS. 1 to 5. FIG. 1 schematically shows the internal arrangement of a bending portion 2 arranged at the distal end portion of an insertion portion 3 of an endoscope as a flexible tube.

Referring to FIG. 1, reference numeral 4 denotes a distal end portion of an endoscope which is disposed at the distal end side of the bending portion 2. An objective lens 6 and an illumination lens 8 are disposed on the distal end portion 4. In addition, the distal end opening portion of a forceps channel 10 is formed in the distal end portion 4.

The distal end portion of an image guide fiber (not shown) or a CCD (charge coupled device) is arranged to oppose the rear surface of the objective lens 6. The distal end portion of a light guide fiber (not shown) or a small lamp is arranged to oppose the rear surface of the illumination lens 8.

Either the image guide fiber or a CCD cable (not shown), and either the light guide fiber or a lamp cable (not shown) are disposed in the flexible tube of the insertion portion 3 of the endoscope. In addition, an operating portion 56 (to be described later) for the bending portion 2, a flexible tube winding drum (not shown), and the like are arranged on the proximal end side of the flexible tube, i.e., the manual operating portion side of the endoscope.

A plurality of bending pieces 12 are arranged in the bending portion 2 along its axis direction. As shown in FIG. 2B, each pair of adjacent bending pieces 12 are pivotally coupled to each other through a pair of rivets 26. That is, the second bending piece 12 adjacent to a first bending piece 12a at the distal end is coupled to the first bending piece 12a to be freely pivoted about one pair of rivets 26, disposed at the upper and lower positions in FIG. 3A, in the lateral direction in FIG. 3A, thus forming a first coupling portion which is pivoted in the lateral direction.

Figure 3A:
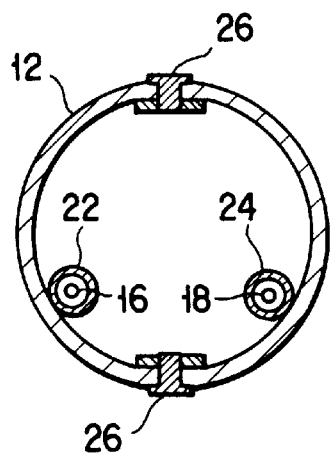
FIG. 3A is a sectional view taken along a line 3A—3A in FIG. 2B.
Figure 3B:
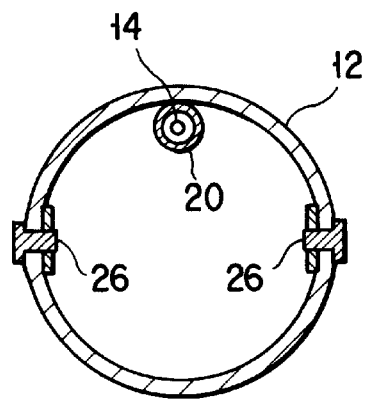
FIG. 3B is a sectional view taken along a line 3B—3B in FIG. 2B.

The third bending piece 12 adjacent to the second bending piece 12 is coupled the second bending piece 12 to be freely pivoted about one pair of rivets 26, disposed at the left and right positions in FIG. 3B, in the vertical direction in FIG. 3B, thus forming a second coupling portion which is pivoted in the vertical direction.

Note that the axis (pivot axis) between the pair of rivets 26 of the first coupling portion is perpendicular to the axis (pivot axis) between the pair of rivets 26 of the second coupling portion. First and second coupling portions, each having the same arrangement as that described above, are alternately arranged between the plurality of bending pieces 12 arranged along the axial direction.

Either a first cylindrical wire holder 20 (see FIG. 3B) for holding a first angle wire 14 (to be described later) or second and third cylindrical wire holders 22 and 24 (see FIG. 3A) for respectively holding second and third angle wires 16 and 18 are fixed to the inner surface of each bending piece 12 in the bending portion 2 by a means such as brazing at one or two of three positions, on the inner circumference of each bending piece 12, each of which is equidistant from adjacent positions.

In this case, as shown in FIG. 3A, the second and third wire holders 22 and 24 through which the second and third angle wires 16 and 18 can be inserted are fixed to the inner surface of the second bending piece 12 coupled to the first bending piece 12a adjacent to the distal end portion 4 so as to be respectively located on axes symmetrical about the axis between the pair of rivets 26 of the first coupling portion.

As shown in FIG. 3B, the first wire holder 20 through which the first angle wire 14 can be inserted is fixed to the inner surface of the third bending piece 12 coupled to the second bending piece 12 so as to be located on an axis perpendicular to the axis between the pair of rivets 26 of the second coupling portion. The plurality of bending pieces 12 arranged along the axial direction are alternately combined in the above-described manner.

Figure 2A:
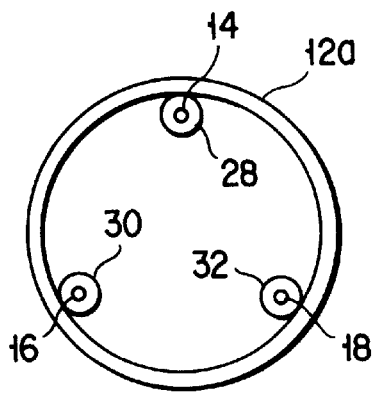
FIG. 2A is a front view schematically showing the arrangement of a bending piece at the distal end.
Figure 2B:
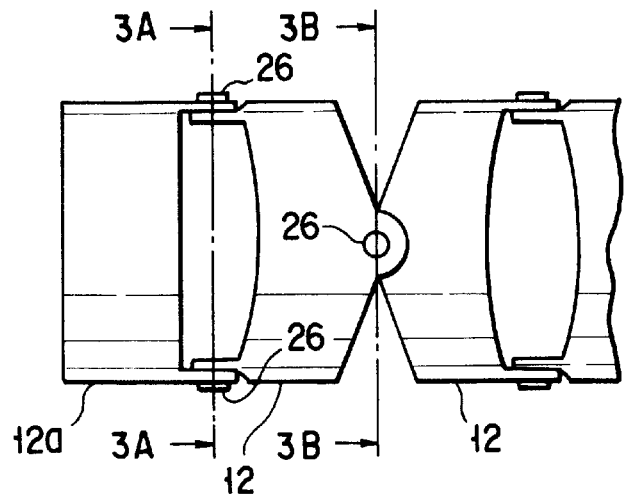
FIG. 2B is a side view showing a state in which the bending piece at the distal end is coupled to its adjacent bending piece.

In addition, as shown in FIG. 2A, first to third fixing portions 28, 30, and 32 to which the distal ends of the first to third angle wires 14, 16, and 18 (see FIG. 1) can be fixed are attached to the inner surface of the first bending piece 12a by, e.g., brazing at three positions, on the inner circumference of the first bending piece 12a, each of which is equidistant from adjacent positions. The distal ends of the first to third angle wires 14, 16, and 18 inserted through the first to third wire holders 20, 22, and 24 in the above-described plurality of bending pieces 12 are respectively fixed to the first to third fixing portions 28, 30, and 32.

The proximal ends of the first to third angle wires 14, 16, and 18 are respectively connected/fixed to the distal ends of first to third pneumatic type artificial rubber muscles (actuators) 34, 36, and 38 disposed in a soft portion constituting an elongated flexible tube portion of the insertion portion connected to the operating portion (not shown) of the endoscope. The first to third artificial rubber muscles 34, 36, and 38 each includes an elastic tube $T_1$, and a netlike tube (braid) $T_2$ formed by winding wires around the outer surface of the elastic tube $T_1$ in the form of a net. The proximal ends of the first to third artificial rubber muscles 34, 36, and 38 are fixed in the insertion portion 3 and are respectively connected to the distal end portions of first to third pressure paths 40, 42, and 44 to communicate therewith.

The proximal end portions of the first to third pressure paths 40, 42, and 44 are connected to a driving circuit (see FIG. 5) (to be described later) for the artificial rubber muscles 34, 36, and 38 to communicate therewith. Suction/evacuation effects produced by the driving circuit directly act on the first to third artificial rubber muscles 34, 36, and 38 through the first to third pressure paths 40, 42, and 44.

More specifically, in the case of suction, the elastic tubes $T_1$ of the artificial rubber muscles 34, 36, and 38 are elastically deformed while they are influenced by the wires of the braids $T_2$. As a result, the first to third artificial rubber muscles 34, 36, and 38 expand in the radial direction and contract in the axial direction, thus pulling the first to third angle wires 14, 16, and 18. In the case of evacuation, the first to third artificial rubber muscles 34, 36, and 38 contract in the radial direction and expand in the axial direction, thus reducing the pulling forces of the first to third angle wires 14, 16, and 18.

FIG. 5 is a block diagram showing a driving circuit for the artificial rubber muscles 34, 36, and 38. As shown in FIG. 5, the first to third artificial rubber muscles 34, 36, and 38 are connected to a compressor 52 through first to third proportioning control valves 46, 48, and 50, each capable of adjusting the valve opening. The first to third proportioning control valves 46, 48, and 50 are connected to a control circuit 54. The operating portion 56 such as a joystick for controlling a bending operation (bending direction and bending amount) of the bending portion 2 is connected to the control circuit 54. Suction/evacuation operations of the first to third artificial rubber muscles 34, 36, and 38 are independently controlled by the control circuit 54 on the basis of commands output from the operating portion 56.

An operation of the bending operation apparatus for the tubular insertion member according to this embodiment will be described below. When the operating portion 56 is operated in the upward (UP) direction, the control circuit 54 is driven in accordance with an output signal from the operating portion 56 to set only the first proportioning control valve 46 at an opening corresponding to the operating amount of the operating portion 56, e.g., in a substantially fully open state. With this operation, as shown in FIG. 4, a proper amount of compressed air supplied from the compressor 52 is fed into the first artificial rubber muscle 34 through the first pressure path 40, thus causing the first artificial rubber muscle 34 to expand in the radial direction and contract in the axial direction. As a result, only the first angle wire 14 is pulled to bend the bending portion 2 in the UP direction.

When the operating portion 56 is operated in the downward (DOWN) direction, the control circuit 54 is driven in accordance with an output signal from the operating portion 56. The first artificial rubber muscle 34 is controlled in accordance with a control signal from the control circuit 54 to be in a non-pressurized state, while the second and third proportioning control valves 48 and 50 are set at an opening corresponding to the operating amount of the operating portion 56, e.g., in a substantially fully open state. With this operation, compressed air supplied from the compressor 52 is evenly fed into the second and third artificial rubber muscles 36 and 38 through the second and third pressure paths 42 and 44, thus causing the second and third artificial rubber muscles 36 and 38 to expand in the radial direction and contract in the axial direction. As a result, the second and third angle wires 16 and 18 are evenly pulled to bend the bending portion 2 in the DOWN direction.

When the operation portion 56 is operated in the right (RIGHT) direction, the control circuit 54 is driven in accordance with an output signal from the operating portion 56. The first, second, and third proportioning control valves 46, 48, and 50 are switched/operated in accordance with a control signal from the control circuit 54 to set the third artificial rubber muscle 38 in a non-pressurized state and respectively set the first and second proportioning control valves 46 and 48 at proper openings. At this time, as shown in FIG. 4, the second proportioning control valve 48 is set at an opening smaller than the opening corresponding to the fully open state, and the opening of the first proportioning control valve 46 is set to be smaller than that of the second proportioning control valve 48. For this reason, compressed air supplied from the compressor 52 is fed into the second artificial rubber muscle 36 in a large amount, while a small amount of compressed air is fed into the first artificial rubber muscle 34 to inhibit the bending portion 2 from moving downward, as shown in FIG. 4. As a result, the bending portion 2 is bent parallel to the RIGHT direction.

When the operating portion 56 is operated in the left (LEFT) direction, the control circuit 54 is driven in accordance with an output signal from the operating portion 56. The first, second, and third proportioning control valves 46, 48, and 50 are switched/operated in accordance with a control signal from the control circuit 54 to set the second artificial rubber muscle 36 in a non-pressurized state and respectively set the first and third proportioning control valves 46 and 50 at proper openings. At this time, the third proportioning control valve 50 is set at an opening smaller than the opening corresponding to the fully open state, and the opening of the first proportioning control valve 46 is set to be smaller than that of the third proportioning control valve 50. For this reason, compressed air supplied from the compressor 52 is fed into the third artificial rubber muscle 38 in a large amount, while a small amount of compressed air is fed into the first artificial rubber muscle 34 to inhibit the bending portion 2 from moving downward, as shown in FIG. 4. As a result, the bending portion 2 is bent in the LEFT direction.

When the operating portion 56 is operated in an intermediate direction between the UP and RIGHT directions, i.e., the UR direction, the control circuit 54 is driven in accordance with an output signal from the operating portion 56. The first, second, and third proportioning control valves 46, 48, and 50 are switched/operated in accordance with a control signal from the control circuit 54 to set the third artificial rubber muscle 38 in a non-pressurized state and respectively set the first and second proportioning control valves 46 and 48 at proper openings. At this time, the first proportioning control valve 46 is set at an opening smaller than the opening corresponding to the fully open state, and the opening of the second proportioning control valve 48 is set to be smaller than that of the first proportioning control valve 46. For this reason, compressed air supplied from the compressor 52 is fed into the first artificial rubber muscle 34 in a large amount, while a small amount (enough to bend the bending portion 2 in the UR direction by using a synthetic force generated by the first and second artificial rubber muscles 34 and 36) of compressed air is fed into the second artificial rubber muscle 36, as shown in FIG. 4. As a result, the bending portion 2 is bent in the UR direction with high precision.

When the operating portion 56 is operated in an intermediate direction between the UP and LEFT directions, i.e., the UL direction, the control circuit 54 is driven in accordance with an output signal from the operating portion 56. The first, second, and third proportioning control valves 46, 48, and 50 are switched/operated in accordance with a control signal from the control circuit 54 to set the second artificial rubber muscle 36 in a non-pressurized state and respectively set the first and third proportioning control valves 46 and 50 at proper openings. At this time, the first proportioning control valve 46 is set at an opening smaller than that opening corresponding to the fully open state, and the opening of the third proportioning control valve 50 is set to be smaller than that of the first proportioning control valve 46. For this reason, compressed air supplied from the compressor 52 is fed into the first artificial rubber muscle 34 in a large amount, while a small amount (enough to bend the bending portion 2 in the UL direction by using a synthetic force generated by the first and third artificial rubber muscles 34 and 38) of compressed air is fed into the third artificial rubber muscle 38, as shown in FIG. 4. As a result, the bending portion 2 is bent in the UL direction with high precision.

When the operating portion 56 is operated in an intermediate direction between the DOWN and RIGHT direction, i.e., the DR direction, the control circuit 54 is driven in accordance with an output signal from the operating portion 56. The first, second, and third proportioning control valves 46, 48, and 50 are switched/operated in accordance with a control signal from the control circuit 54 to set the first artificial rubber muscle 34 in a non-pressurized state and respectively set the second and third proportioning control valves 48 and 50 at proper openings. At this time, the second proportioning control valve 48 is set at an opening smaller than the opening corresponding to the fully open state, while the opening of the third proportioning control valve 50 is set to be smaller than that of the second proportioning control valve 48. For this reason, compressed air supplied from the compressor 52 is fed into the second artificial rubber muscle 36 in a large amount, while a small amount (enough to bend the bending portion 2 in the DR direction by using a synthetic force generated by the second and third artificial rubber muscles 36 and 38) of compressed air is fed into the third artificial rubber muscle 38. As a result, the bending portion 2 is bent in the DR direction with high precision.

Lastly, when the operating portion 56 is operated in an intermediate direction between the DOWN and LEFT directions, i.e., the DL direction, the control circuit 54 is driven in accordance with an output signal from the operating portion 56. The first, second, and third proportioning control valves 46, 48, and 50 are switched/operated in accordance with a control signal from the control circuit 54 to set the first artificial rubber muscle 34 in a non-pressurized state and respectively set the second and third proportioning control valves 48 and 50 at proper openings. At this time, the third proportioning control valve 50 is set at an opening smaller than the opening corresponding to the fully open state, while the opening of the second proportioning control valve 48 is set to be smaller than that of the third proportioning control valve 50. For this reason, compressed air supplied from the compressor 52 is fed into the third artificial rubber muscle 38 in a large amount, while a small amount (enough to bend the bending portion in the DL direction by using a synthetic force generated by the second and third artificial rubber muscles 36 and 38) of compressed air is fed into the second artificial rubber muscle 36. As a result, the bending portion 2 is bent in the DL direction with high precision.

Although the above-described operations are associated with typical bending directions, the bending portion 2 can be bent in an arbitrary direction by switching/setting the openings of the first, second, and third proportioning control valves 46, 48, and 50 to change the ratio between the pressures acting on the first, second, and third artificial rubber muscles 34, 36, and 38. In addition, an arbitrary bending amount can be achieved by changing the pressures on the respective artificial rubber muscles while keeping the ratio between the pressures constant.

As described above, the bending operation apparatus of this embodiment is designed such that the first to third angle wires 14, 16, and 18 arranged at three positions, on the inner circumference of each bending piece 12 in the bending portion 2, each of which is equidistant from adjacent positions are properly pulled by the first and third artificial rubber muscles 34, 36, and 38, respectively. Therefore, the bending portion 2 can be bent in an arbitrary direction, and a reduction in the diameter of the flexible tube can be achieved.

In addition, the first to third angle wires 14, 16, and 18 are disposed in the bending portion 2 having a relatively complicated arrangement, while the first to third pneumatic type artificial rubber muscles 34, 36, and 38 are disposed in the insertion portion 3 which is simpler in arrangement than the bending portion 2. Therefore, interference between each bending piece 12 of the bending portion 2 and the first to third artificial rubber muscles 34, 36, and 38 can be reliably prevented during a bending operation of the bending portion 2, thus stabilizing the bending operation of the bending portion 2.

Note that general ON/OFF type solenoid valves may be used in place of the proportioning control valves of the embodiment so that the solenoid valves are opened/closed by pulses, and the numbers of pulses are controlled by a control circuit.

In the above embodiment, the first to third angle wires 14, 16, and 18 and the first to third wire holders 20, 22, and 24 are arranged at three positions, on the inner circumference of each bending piece 12, each of which is equidistant from adjacent positions. However, the first to third angle wires 14, 16, and 18 and the first to third wire holders 20, 22, and 24 may be arranged at positions slightly shifted from the three positions each of which is equidistant from adjacent positions.

If the first to third angle wires 14, 16, and 18 and the first to third wire holders 20, 22, and 24 are arranged at positions shifted from the three equidistant angular positions, a bending operation can be accurately performed in the four directions, i.e., the upward, downward, left, and right directions, and other arbitrary directions by controlling the ratio between the pulling forces of the first, second, and third artificial rubber muscles 34, 36, and 38.

The second embodiment of the present invention will be described next with reference to FIGS. 6 to 8A. The same reference numerals in the second embodiment denote the same parts as in the first embodiment, and a description thereof will be omitted.

A bending operation apparatus of this embodiment uses first to third SMA (shape memory alloy) wires 58, 60, and 62 as actuators for pulling first and third angle wires 14, 16, and 18, as shown in FIGS. 6 to 8A.

Each of the SMA wires 58, 60, and 62 is constituted by a bidirectional SMA such as an NiTi alloy. If each of the SMA wires 58, 60, and 62 is heated to the critical temperature or more, its length is decreased. In contrast to this, if each SMA wire is cooled to a temperature below the critical temperature, its length is increased to the original length.

Figure 6:
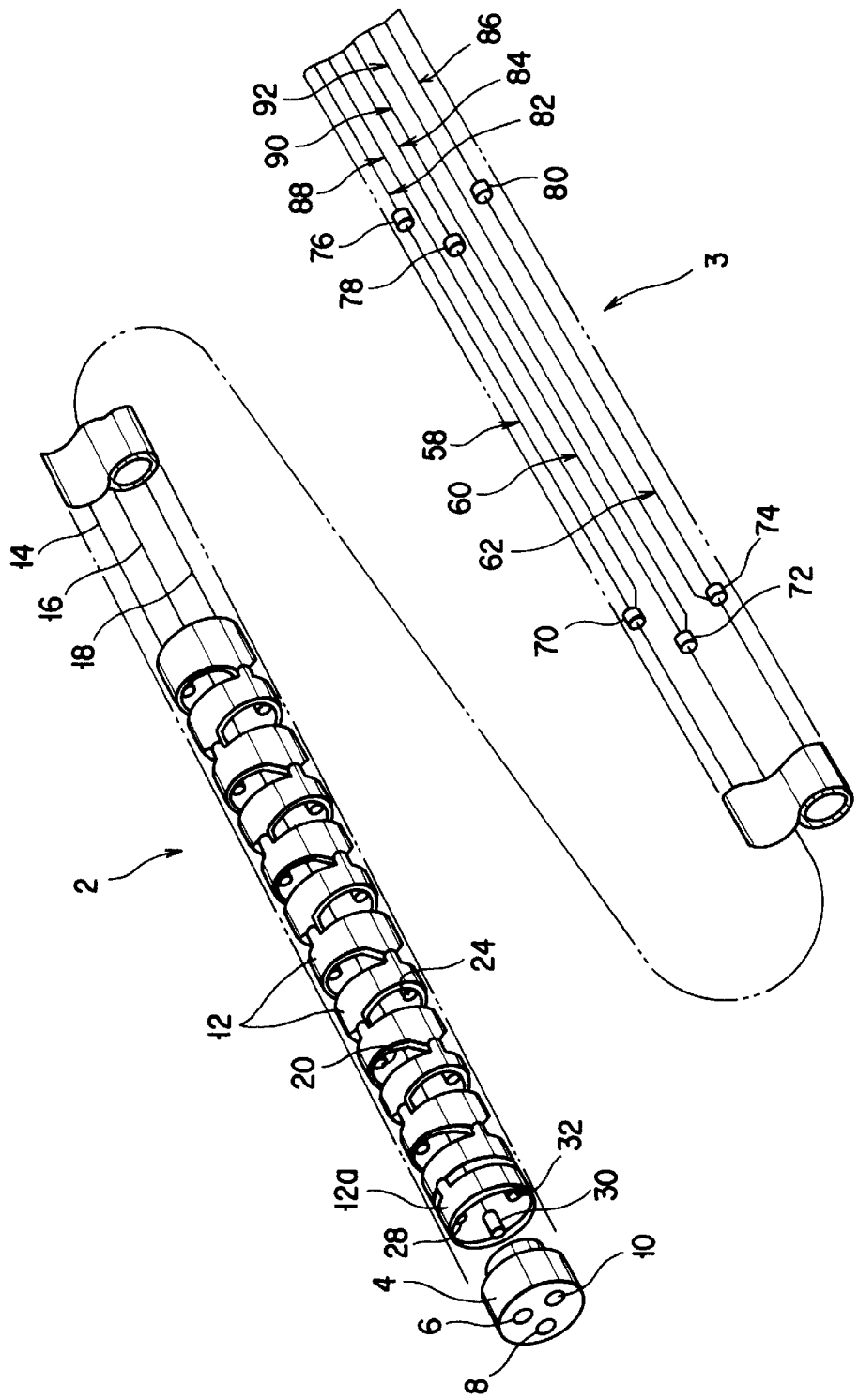
FIG. 6 is a perspective view schematically showing the arrangement of the bending mechanism of a flexible tube according to the second embodiment of the present invention.

The proximal ends of the first to third angle wires 14, 16, and 18 are connected/fixed to the distal ends of the first to third SMA wires 58, 60, and 62, disposed in a insertion portion 3, through first to third connecting portions 70, 72, and 74, respectively, as shown in FIG. 6. The proximal ends of the first to third SMA wires 58, 60, and 62 are connected to the distal end portions of first to third lead wires 82, 84, and 86 through fourth to sixth connecting portions 76, 78, and 80 which are fixed to the insertion portion 3. The distal end portions of fourth to sixth lead wires 88, 90, and 92 are respectively connected to the first to third connecting portions 70, 72, and 74.

The proximal end portions of the first and fourth lead wires 82 and 88 are electrically connected to a first voltage control circuit 64 shown in FIG. 8A, whereas the proximal end portions of the second and fifth lead wires 84 and 90 are electrically connected to a second voltage control circuit 66. In addition, the proximal end portions of the third and sixth lead wires 86 and 92 are electrically connected to a third voltage control circuit 68. A power source circuit 94 and a resistance control circuit 96 are electrically connected to the first to third voltage control circuits 64, 66, and 68.

An operating portion 56 such as a joystick is connected to the resistance control circuit 96. The amounts of voltages applied to the first to third voltage control circuits 64, 66, and 68 are controlled by the resistance control circuit 96 in accordance with an operation signal transmitted from the operating portion 56.

An operation of the bending operation apparatus of this embodiment will be described below. Since the operation of the bending operation apparatus of the second embodiment is almost the same as that of the apparatus of the first embodiment, only a case wherein the joystick as the operating portion 56 is operated in the downward (DOWN) direction will be described as a representative operation, but a description of other cases will be omitted.

When the joystick as the operating portion 56 is operated in the downward (DOWN) direction, the resistance control circuit 96 is driven in accordance with an output signal from the operating portion 56. The first to third voltage control circuits 64, 66, and 68 are controlled by a control signal from the resistance control circuit 96. In this case, the SMA wire 58 is held in a deenergized state by the first voltage control circuit 64 (i.e., the voltage applied to the first SMA wire 58 through the first and fourth lead wires 82 and 88 is withdrawn), while voltages are evenly applied from the power source circuit 94 to the second and third SMA wires 60 and 62 upon operation of the second and third voltage control circuits 66 and 68. With this operation, as shown in FIG. 7, the second and third SMA wires 60 and 62 are evenly heated, and their lengths are decreased. As a result, the second and third angle wires 16 and 18 are evenly pulled, and a bending portion 2 is bent in the DOWN direction.

The bending operation apparatus of the second embodiment is also designed such that the first to third angle wires 14, 16, and 18 arranged at three positions, on the inner circumference of each bending piece 12 in the bending portion 2, each of which is equidistant from adjacent positions, are properly pulled by the first to third SMA wires 58, 60, and 62, respectively. Therefore, similar to the first embodiment, in the second embodiment, the bending portion 2 can be bent in an arbitrary direction, and a reduction in the diameter of the flexible tube can be achieved.

In addition, the first to third angle wires 14, 16, and 18 are arranged in the bending portion 2 having a relatively complicated arrangement, whereas the first to third SMA wires 58, 60, and 62 are arranged in the soft portion 3 which is simpler in arrangement than the bending portion 2. That is, the first to third SMA wires 58, 60, and 62 need not be insulated in the bending portion 2 having a relatively complicated arrangement. This arrangement is advantageous in reducing the overall diameter of an insertion portion 3 of an endoscope.

Note that, as shown in FIG. 7, not only the bending direction of the bending portion 2 can be arbitrarily set by changing the ratio between the heating amounts of the first to third SMA wires 58, 60, and 62, but also the bending amount itself can be changed by changing the energization amounts (voltages, pulse widths, or duty ratios) while keeping the ratio of the heating amounts of the first to third SMA wires 58, 60, and 62 constant.

Figure 8B:
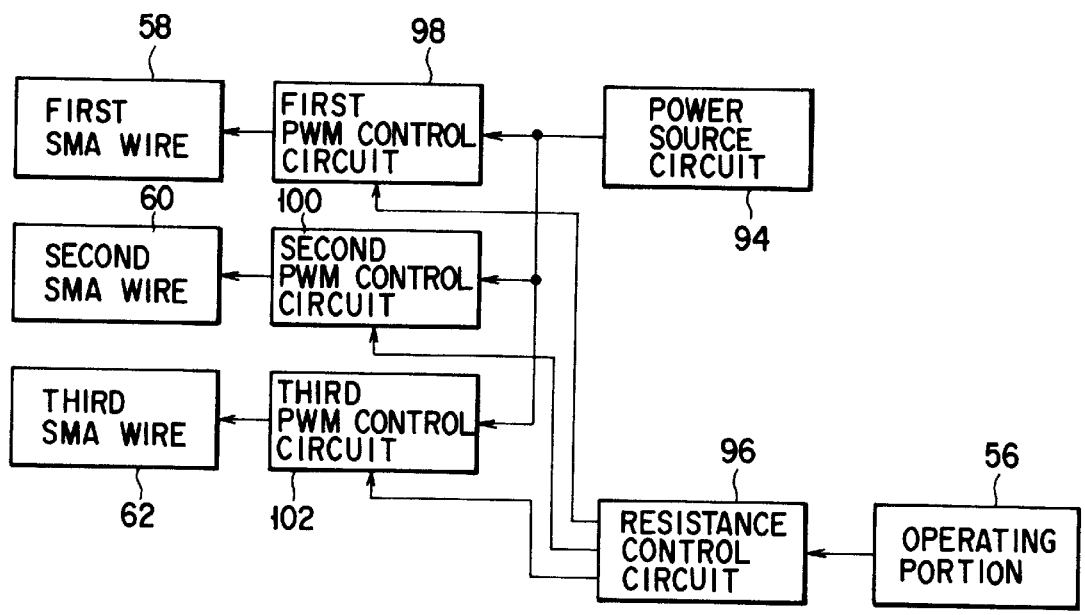
FIG. 8B is a block diagram showing a modification of the driving circuit.

In addition, the driving circuit shown in FIG. 8B can be used as a modification of the driving circuit used in the second embodiment. More specifically, in this modification, first to third PWM control circuits 98, 100, and 102 are arranged in place of the first to third voltage control circuits 64, 66, and 68. According to the driving circuit of this modification, the heating amounts of first to third SMA wires 58, 60, and 62 are controlled by pulse-width modulation.

Figure 9:
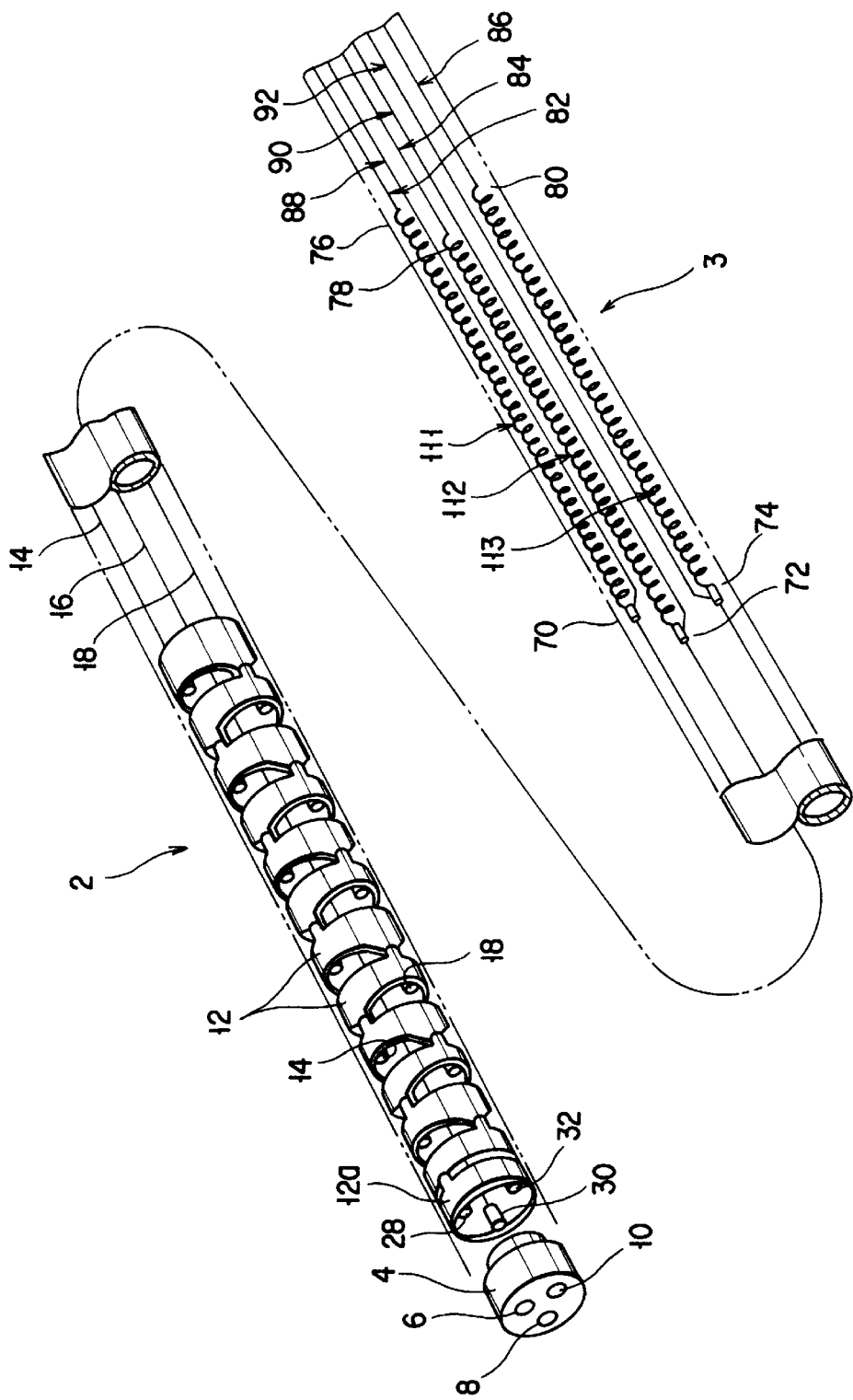
FIG. 9 is a perspective view showing a modification of the second embodiment of the present invention.

FIG. 9 shows a modification of the second embodiment. In this modification, bidirectional SMA wire coils 111, 112, and 113 are used in place of the first to third SMA wires 58, 60, and 62.

A closely wound shape is prestored in each of the SMA coils 111, 112, and 113. When the SMA coils 111, 112, and 113 are mounted in an endoscope, they are pulled/deformed and hence are mounted in the endoscope in a loosely wound state.

When the SMA coils 111, 112, and 113 are energized and heated, each coil contracts a closely wound shape to pull the first to third angle wires 14, 16, and 18. When the SMA coils 111, 112, and 113 are deenergized, each coil is deformed into the original state, i.e., the loosely wound state caused by the pulling force, thus releasing the bending operation of a bending portion 2.

A bending operation apparatus for a tubular insertion member according to the third embodiment of the present invention will be described below with reference to FIGS. 10 to 14. The same reference numerals in the third embodiment denote the same parts as in the first embodiment, and a description thereof will be omitted.

Figure 10:
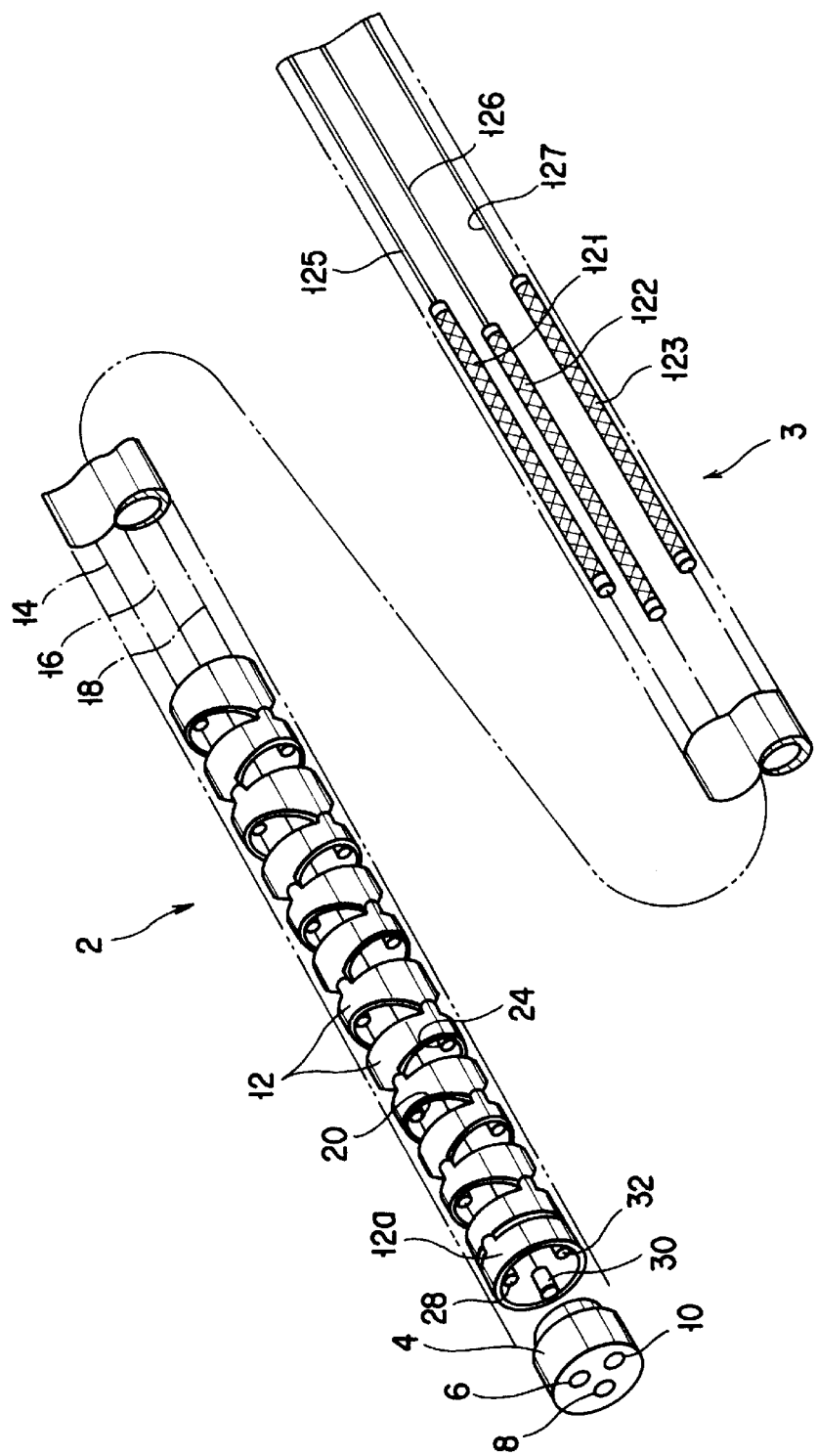
FIG. 10 is a perspective view schematically showing the arrangement of the bending mechanism of a flexible tube according to the third embodiment of the present invention.

As shown in FIG. 10, the proximal ends of first to third angle wires 14, 16, and 18 are connected/fixed to the distal ends of first to third fluid pressure driven artificial rubber muscles (actuators) 121, 122, and 123 disposed in a soft portion 3 of an endoscope.

Each of the first to third artificial rubber muscles 121, 122, and 123 includes an elastic tube and a net-like tube (braid) formed on the outer surface of the elastic tube. The proximal ends of the first to third artificial rubber muscles 121, 122, and 123 are fixed in the soft portion 3 and are respectively connected to the distal end portions of first to third energization cables 125, 126, and 127. The proximal end portions of the first to third energization cables 125, 126, and 127 are connected to a driving circuit (see FIG. 14) which will be described later.

Since the first to third artificial rubber muscles 121, 122, and 123 have the same structure, only the first artificial rubber muscle 121 will be described below for the descriptive convenience. As shown in FIGS. 11(a) and 11(b), the first artificial rubber muscle 121 has an elastic tube 129 inside a net-like tube 128. The two ends of the elastic tube 129 are respectively bonded to mouthpieces 130 and 131 and are fixed thereto by winding strings. The proximal end of the first angle wire 14 is connected to the mouthpiece 130.

The elastic tube 129 is filled with a thermal expansion material 132 such as paraffin or wax whose volume is increased with an increase in temperature. In addition, a first coil heater 133 is housed in the elastic tube 129. The first heater 133 is connected to the distal end portion of the first energization cable 125.

Similarly, a second heater 134 shown in FIG. 14 is housed in the second artificial rubber muscle 122, and a third heater 135 is housed in the third artificial rubber muscle 123. The second and third heaters 134 and 135 are respectively connected to the second and third energization cables 126 and 127.

As shown in FIG. 14, the first to third energization control circuits 136, 137, and 138 are respectively connected to the first to third heaters 133, 134, and 135 and a power source section 139. The first to third energization control circuits 136, 137, and 138 are connected to a control circuit 141. An operating portion 140 such as a joystick for controlling a bending operation (bending direction and bending amount) of the bending portion 2 is connected to the control circuit 141. An operation signal from the operating portion 140 is sent to the control circuit 141 to control the energization control circuits 136, 137, and 138.

An operation of the bending operation apparatus for the tubular insertion member according to the third embodiment will be described next. Since the operation of the bending operation apparatus of the third embodiment is almost the same as that of the apparatus of the first embodiment, only a case wherein the joystick as the operating portion 140 is operated in the downward (DOWN) direction will be described below, but a description of other cases will be omitted.

When the joystick as the operating portion 140 is operated in the downward (DOWN) direction, the control circuit 141 is driven in accordance with an output signal from the operating portion 140. The first to third energization control circuits 136, 137, and 138 are controlled by a control signal from the control circuit 141. In this case, the first heater 133 is held in a deenergized state by the first energization control circuit 136, while the second and third heaters 134 and 135 are energized upon operation of the second and third energization control circuits 137 and 138.

With this operation, the thermal expansion materials 132 in the second and third artificial rubber muscles 122 and 123 are respectively heated by the second and third heaters 134 and 135, and their volumes are increased, thus increasing the internal pressures of the second and third artificial rubber muscles 122 and 123, as shown in FIG. 13. As a result, the second and third artificial rubber muscles 122 and 123 expand in the radial direction and contract in the axial direction, and the second and third angle wires 16 and 18 are evenly pulled, thus bending the bending portion 2 in the DOWN direction.

If, as shown in FIG. 11(a), the length of each of the artificial rubber muscles 121, 122, and 123 during a non-heating period is represented by l, and a contraction amount upon expansion is represented by x, a coefficient of contraction is given by x/l. In addition, if the coefficient of cubical expansion of the thermal expansion material 132 such as paraffin is represented by $\epsilon$, the relationship between a heating temperature T, $\epsilon$, and x/l can be represented by the graph in FIG. 12. Therefore, actuators having various temperature coefficients can be formed by precisely adjusting the temperature expansion coefficient and melting point of the thermal expansion material 132.

The bending mechanism of a flexible tube according to the fourth embodiment of the present invention will be described next with reference to FIGS. 15 to 16(b). FIG. 15 shows a schematic arrangement of an endoscope 201. Three actuators 204 are arranged behind a bending portion 203 in an insertion portion 202 of the endoscope 201.

The distal end portions of three angle wires 206 are fixed to a distal end portion 205 of the insertion portion 202. The proximal end portion of each of the angle wires 206 is coupled to a corresponding one of the actuators 204. Note that the bending portion 203 is constituted by a plurality of joint pieces 207 arranged along the axial direction. The positional relationship between the angle wires 206, the bending portion 203, and the actuators 204 is the same as that in the first embodiment.

An operating switch 209 is arranged on an operating portion 208. A connector 211 of a universal cable 210 is detachably coupled to a light source unit 212. In addition, an energization control section 213 and a power source section 214 are arranged in the light source unit 212.

FIGS. 16(a) and 16(b) show a schematic arrangement of the actuator 204. A filter 216 is disposed on one end side in a casing 215 of the actuator 204. The casing 215 is partitioned into two chambers by this filter 216.

A hydrogen storage alloy 217 and a hydrogen storage alloy heater 221 are housed in one of the chambers in the casing 215. An expandable bellows 218 is housed in the other chamber in the casing 215.

One end of an operating rod 220 is fixed to the distal end portion of the bellows 218. The other end of the operating rod 220 extends outside through a through hole formed in the opposite wall of the casing 215. The proximal end portion of the angle wire 206 is connected to the extending end portion of the operating rod 220.

A coil spring 219 for biasing the bellows 218 in the direction of expansion is disposed in the bellows 218. In addition, one end of a lead wire 222 is connected to the hydrogen storage alloy heater 221. The other end of the lead wire 222 is connected to the energization control section 213 in the light source unit 212.

In the above-described arrangement, when the hydrogen storage alloy 217 is heated by the heater 221, hydrogen gas is emitted from the hydrogen storage alloy 217 into the housing chamber of the bellows 218 in the casing 215. With this operation, since the internal pressure of the housing chamber of the bellows 218 is increased, the state of the bellows 218 is changed in the direction of contraction, i.e., from the state shown in FIG. 16(a) to the state shown in FIG. 16(b). Upon this contraction of the bellows 218, the operating rod 220 is pushed out to the left, as shown in FIG. 16(b), and the angle wire 206 is pushed out.

When the heater 221 is turned off to cause the hydrogen storage alloy 217 to dissipate, the hydrogen gas in the housing chamber of the bellows 218 is absorbed by the hydrogen storage alloy 217, and the state shown in FIG. 16(a) is restored.

In a neutral period, during which the three actuators 204 are synchronously operated with the above-described operation to hold the bending portion 3 in a linear state, the heating amounts of the heaters 221 are adjusted to locate the operating rods 220 at a position of X/2 in FIGS. 16(a) and 16(b). Note that a Peltier element may be used in place of the heater 221 to heat/cool the hydrogen storage alloy 217.

Figure 17A:
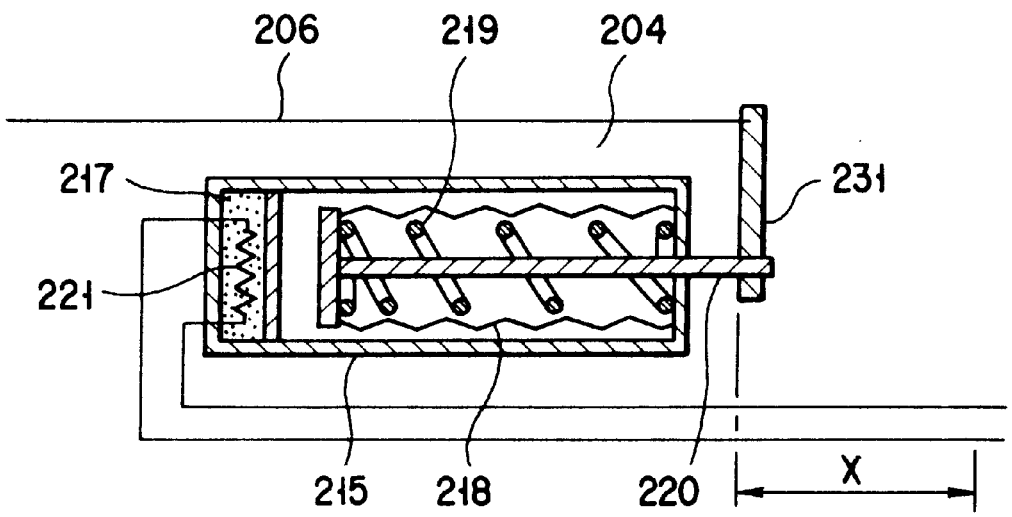
FIGS. 17(a) and 17(b) are views for explaining an operation of an actuator according to the fifth embodiment of the present invention.
Figure 17B:
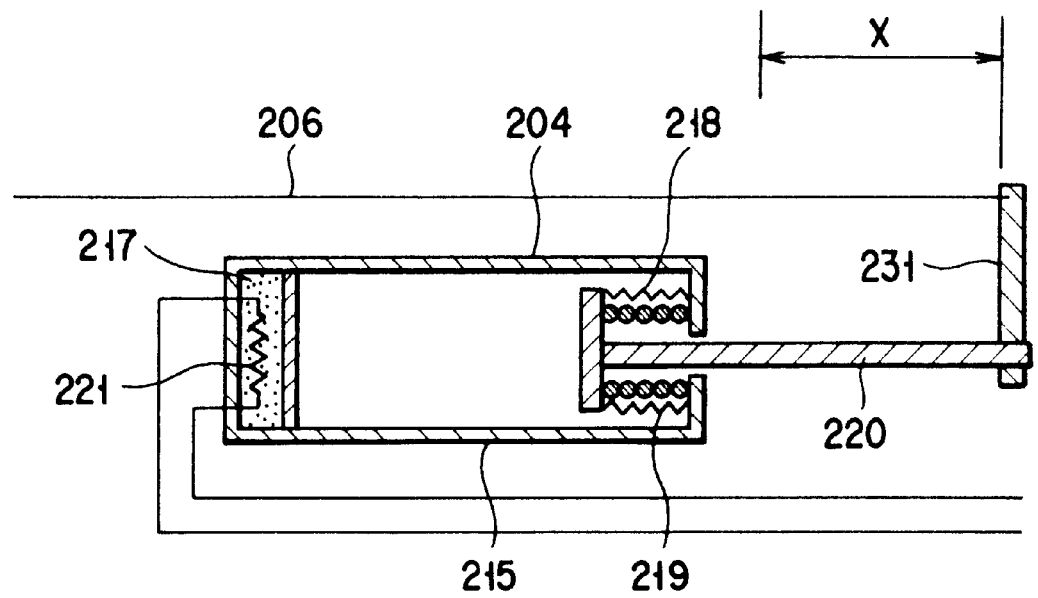
Figure 20A:
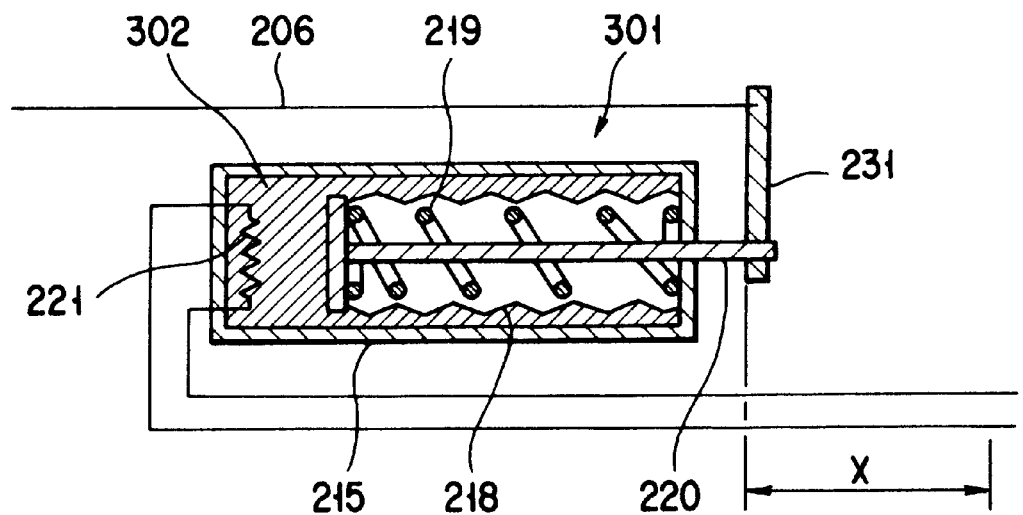
FIGS. 20(a) and 20(b) are views for explaining an operation of an actuator according to the sixth embodiment.
Figure 20B:
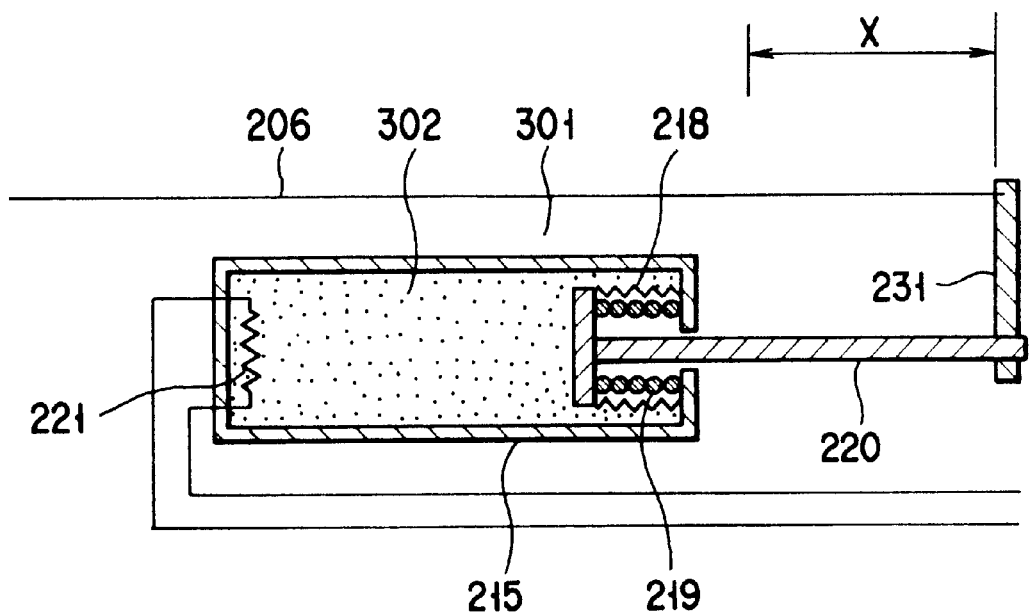

FIGS. 17(a) and 17(b) show the fifth embodiment of the present invention. In this embodiment, unlike the fourth embodiment, the storage chamber of a hydrogen storage alloy 217 is arranged on the distal end portion 205 side in a casing 215 of an actuator 204, and the housing chamber of a bellows 218 is arranged on the operating portion 208 side. In addition, a coupling plate 231 is fixed to the extending end portion of an operating rod 220, and the proximal end portion of an angle wire 206 is connected to the coupling plate 231.

With this arrangement, in the fifth embodiment, when the actuator 204 is operated, the operating rod 220 is pushed out to the right in FIGS. 17(a) and 17(b) upon contraction of the bellows 218, thus pulling the angle wire 206 through the coupling plate 231.

FIGS. 18 to 20(b) show the sixth embodiment of the present invention. In this embodiment, as shown in FIG. 18, three actuators 301 for bending a bending portion 203 are arranged in an operating portion 208 of an endoscope 201. In this case, as shown in FIG. 19, an operating switch 209 of the operating portion 208 includes an upward (UP) direction button 209a, a down-ward (DOWN) direction button 209b, a right (RIGHT) direction button 209c, and a left (LEFT) direction button 209d.

Instead of the hydrogen storage alloy 217 in the fifth embodiment, a flon 302 is stored in a casing 215 of the actuator 301, and a heater 221 is arranged in the storage chamber of the flon 302.

In the above-described arrangement, the flon 302 in the casing 215 of the actuator 301 is kept in a liquid state while its temperature is low. When the flon is heated by the heater 221, it vaporizes and expands. By utilizing this mechanism, a bending operation of the bending portion 203 can be performed in the same manner as in the fifth embodiment.

Figure 21:
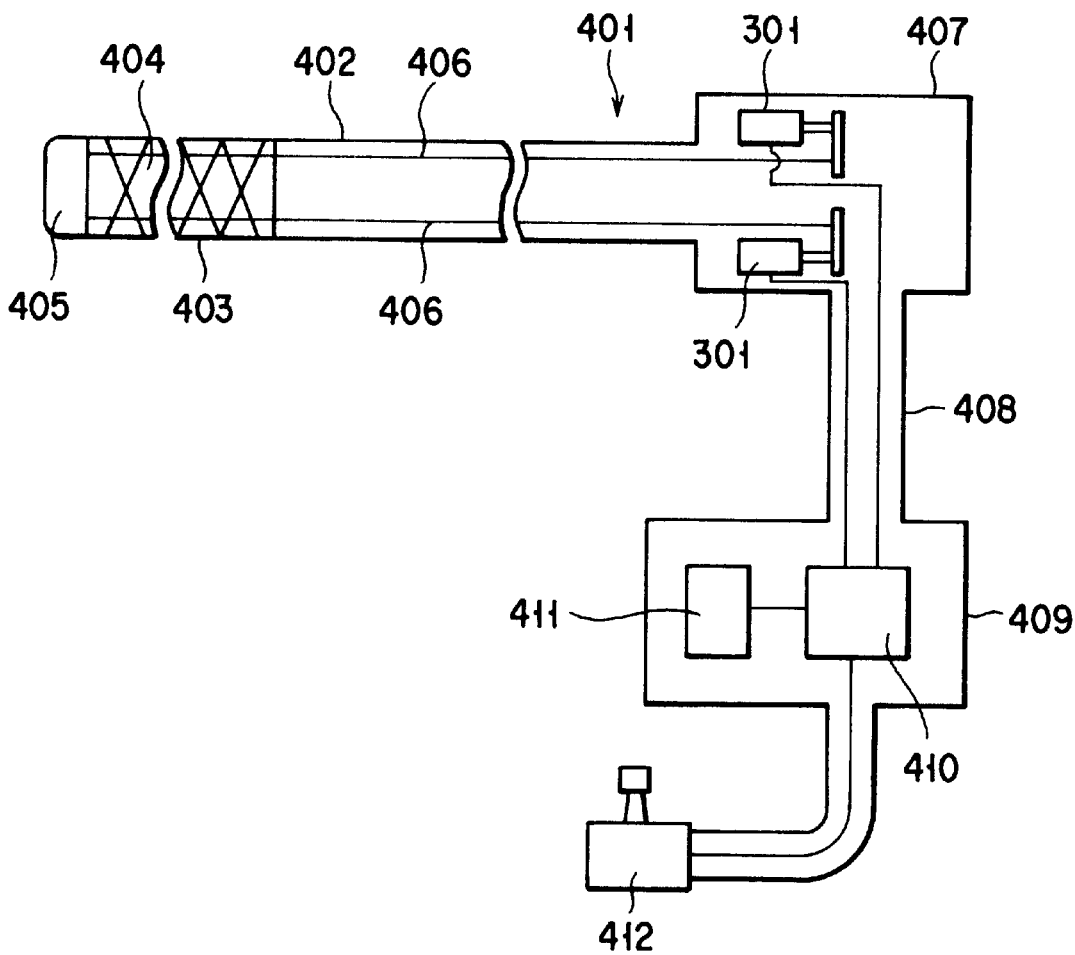
FIG. 21 is a schematic view showing the arrangement of the bending mechanism of a flexible tube according to the seventh embodiment of the present invention.
Figure 22:
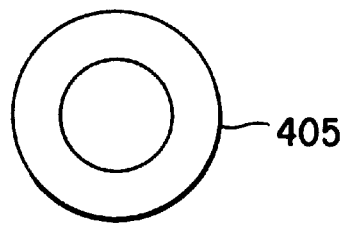
FIG. 22 is a front view of a catheter.

FIGS. 21 and 22 show the seventh embodiment of the present invention. In this embodiment, a catheter 401 is used as a flexible tube of a tubular insertion member. A bending portion 403, which can be bent/deformed, is formed behind a distal end portion 405 of an insertion portion 402 of the catheter 401. The bending portion 403 is constituted by a plurality of joint pieces 404 arranged along the axial direction.

Actuators 301, each having the same arrangement as that in the sixth embodiment, are arranged in an operating portion 407 on the manual operating side of the catheter 401. In this case, ethanol as a thermal expansion material is stored in a casing 215 of the actuator 301 in place of the flon 302 in the sixth embodiment.

The distal end portions of three angle wires 406 are fixed to the distal end portion 405 of the insertion portion 402. The proximal end portions of the respective angle wires 406 are respectively coupled to coupling plates 231 of the actuators 301.

The operating portion 407 is coupled to an external driving unit 409 through cable 408. Furthermore, an energization control section 410 and a power source section 411 are arranged in the driving unit 409. A joystick 412 for a bending operation is connected to the energization control section 410.

In this arrangement, therefore, by operating the operating lever of the joystick 412, the bending portion 403 of the catheter 401 can be bent in the same manner as in the sixth embodiment.

Figure 23:
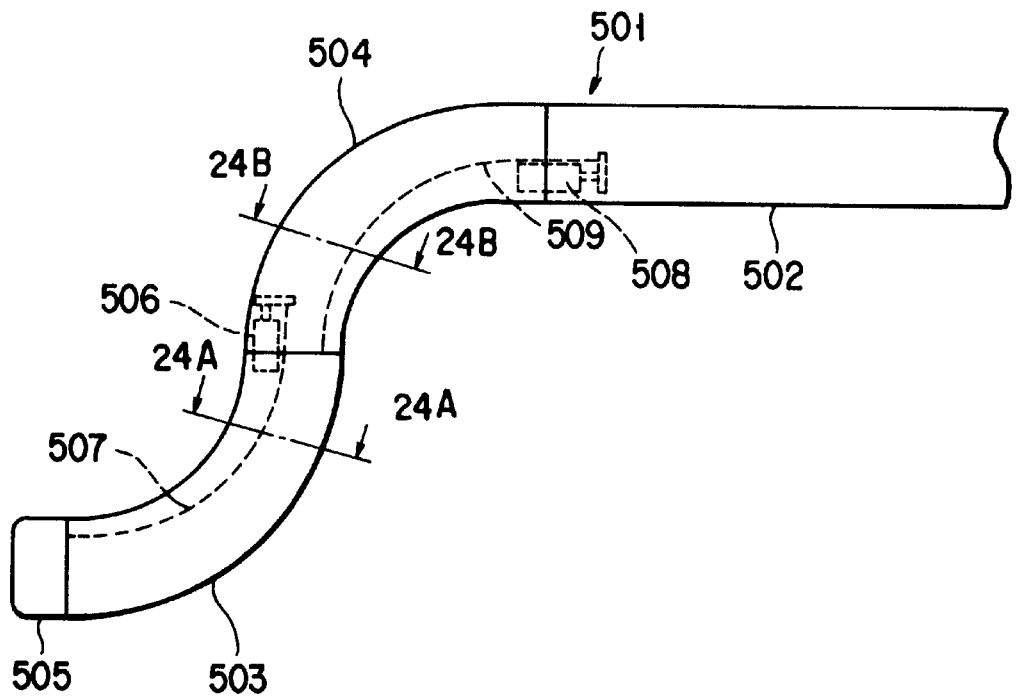
FIG. 23 is a schematic view showing the arrangement of the bending mechanism of a flexible tube according to the eighth embodiment of the present invention.

FIGS. 23 to 26 show the eighth embodiment of the present invention. In this embodiment, as shown in FIG. 23, a two-stage bending type bending mechanism constituted by front and rear bending portions, i.e., first and second bending portions 503 and 504, is formed on the distal end side of an insertion portion 502 of an endoscope 501.

An actuator 506 in the first bending portion 503 on the distal end portion 505 side of the endoscope 501, and an actuator 508 in the second bending portion 504 on the operating portion side have the same arrangement as that of the actuator 301 in the sixth embodiment. In this case, instead of the flon 302 in the sixth embodiment, paraffin is stored in a casing 215 of each of the actuators 506 and 508, and a heater 514 is arranged in the storage chamber of the paraffin.

The actuator 506 in the first bending portion 503 is fixed to the distal end portion of the second bending portion 504. One end of an angle wire 507 is fixed to the distal end portion 505, and the other end of the angle wire 507 is connected to a coupling plate 231 of the actuator 506.

The actuator 508 in the second bending portion 504 is fixed to the distal end portion of the flexible tube of the insertion portion 502. One end of an angle wire 509 is fixed to a joint piece at the proximal end of the first bending portion 503, and the other end of the angle wire 509 is connected to the coupling plate 231 of the actuator 508.

Figures 24A, 24B:
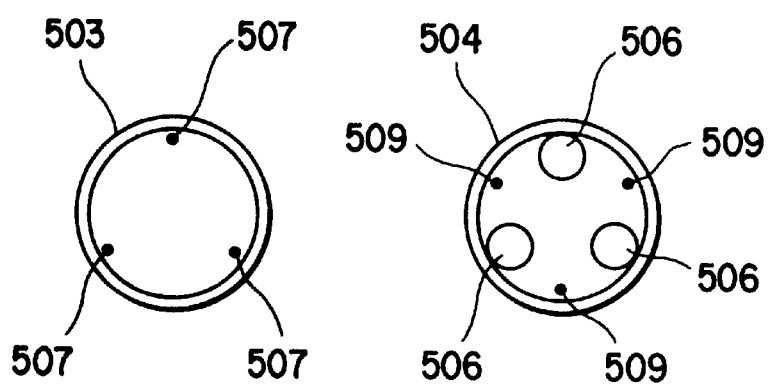
FIG. 24A is a sectional view taken along a line 24A—24A in FIG. 23.
FIG. 24B is a sectional view taken along a line 24B—24B in FIG. 23.

As shown in FIG. 24A, the three actuators 506 and the three angle wires 507 of the first bending portion 503 are arranged at almost equal intervals in the circumferential direction of the first bending portion 503. As shown in FIG. 24B, the three actuators 508 and the three angle wires 509 of the second bending portion 504 are arranged at almost equal intervals in the circumferential direction of the second bending portion 504 so as not to interfere with the three actuators 506 in the first bending portion 503.

Figure 25:
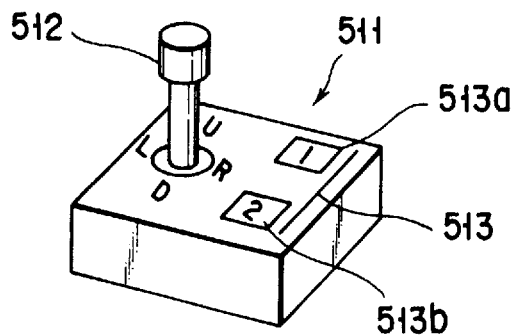
FIG. 25 is a perspective view showing a controller according to the eighth embodiment.

FIG. 25 shows a controller 511 of the two-stage bending type endoscope 501. This controller 511 includes a joystick 512 for controlling bending direction and bending amount, and a switch 513 for selecting either the first bending portion 503 or the second bending portion 504. The selection switch 513 includes a selection button 513a for selecting the first bending portion 503, and a selection button 513b for selecting the second bending portion 504.

Figure 26:
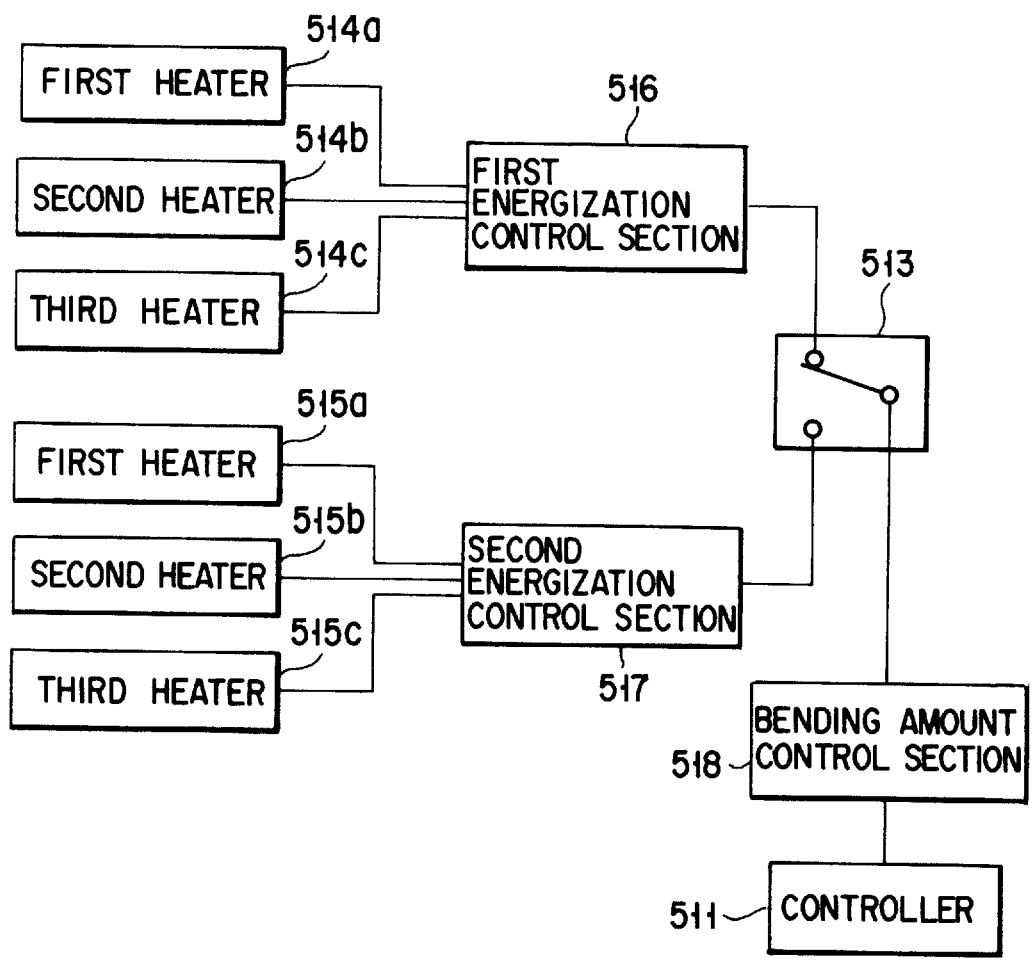
FIG. 26 is a block diagram showing a driving circuit for the bending mechanism according to the eighth embodiment.

As shown in FIG. 26, first to third heaters 514a, 514b, and 514c respectively mounted on the three actuators 506 (the first to third actuators 506a, 506b, and 506c) in the first bending portion 503 are connected to a first energization control section 516 of the controller 511.

Similarly, first to third heaters 515a, 515b, and 515c respectively mounted on the three actuators (first to third actuators 508a, 508b, and 508c) in the second bending portion 504 are connected to a second energization control section 517 of the controller 511.

The first and second energization control sections 516 and 517 are connected to the selection switch 513. The selection switch 513 is connected to the controller 511 through a bending amount control section 518 which is interlocked with an operation of the joystick 512.

In a bending operation of the two-stage bending type endoscope 501, one of the selection buttons 513a and 513b of the selection switch 513 is depressed to select either the first bending portion 503 or the second bending portion 504, and the bending direction and bending amount of the selected first bending portion 503 (or the second bending portion 504) are set upon operation of the joystick 512.

In addition, the energization amounts of the first to third heaters 514a, 514b, and 514c mounted on the first to third actuators 506a, 506b, and 506c in the selected first bending portion 503, or the energization amounts of the first to third heaters 515a, 515b, and 151c mounted on the first to third actuators 508a, 508b, and 508c in the second bending portion 504, are properly set in accordance with the set bending direction and bending amount, thus bending the selected first or second bending portion 503 or 504.

FIGS. 27 and 28 show the ninth embodiment of the present invention. The ninth embodiment is obtained by changing the arrangement of the controller 511 of the two-stage bending type endoscope 501 of the eighth embodiment.

More specifically, as shown in FIG. 27, a controller 521 in this embodiment has a bending operation switch 524 for a second bending portion 504, which switch is arranged on the distal end of a joystick 522 for controlling the bending direction and bending amount of a first bending portion 503.

FIG. 28 shows a driving circuit for the controller 521. In this case, the joystick 522 for the first bending portion 503 and the bending operation switch 524 for the second bending portion 504 are respectively connected to first and second energization control sections 516 and 517. The bending operation switch 524 includes an upward (UP) direction button 524a, a downward (DOWN) direction button 524b, a right (RIGHT) direction button 524c, and left (LEFT) direction button 524d. In addition, a power source section 525 is connected between the first and second energization control sections 516 and 517.

In a bending operation of the two-stage bending type endoscope 501, the bending direction and bending amount of the first bending portion 503 are set upon operation of the joystick 522, and the bending direction and bending amount of the second bending portion 504 are set upon depression of the respective buttons 524a to 524d of the bending operation switch 524. The energization amounts of first to third heaters 514a, 514b, and 514c respectively mounted on first to third actuators 506a, 506b, and 506c in the first bending portion 503, and the energization amounts of first to third heaters 515a, 515b, and 515c respectively mounted on first to third actuators 508a, 508b, and 508c in the second bending portion 504 are properly set in accordance with the set bending directions and bending amounts, thus bending the first and second bending portions 503 and 504.

FIGS. 29 and 30 show the tenth embodiment of the present invention. The tenth embodiment is obtained by further changing the arrangement of the controller 511 of the two-stage bending type endoscope 501 of the eighth embodiment.

More specifically, as shown in FIG. 29, a controller 531 in this embodiment includes a first joystick 532 for controlling the bending direction and bending amount of a first bending portion 503, and a second joystick 533 of a small size, which is arranged on the distal end of the first joystick 532 and is designed to control the bending direction and bending amount of the second bending portion 504. In this case, the first joystick 532 for the first bending portion 503 and the second joystick 533 for the second bending portion 504 are respectively connected to first and second energization control sections 516 and 517.

In a bending operation of the two-stage bending type endoscope 501, the bending direction and bending amount of the first bending portion 503 are set upon operation of the first joystick 532, and the bending direction and bending amount of the second bending portion 504 are set upon operation of the second joystick 533. The energization amounts of first to third heaters 514a, 514b, and 514c respectively mounted on first to third actuators 506a, 506b, and 506c in the first bending portion 503, and the energization amounts of first to third heaters 515a, 515b, and 515c respectively mounted on first to third actuators 508a, 508b, and 508c in the second bending portion 504 are properly set in accordance with the set bending directions and bending amounts, thus bending the first and second bending portions 503 and 504.

Figure 31A:
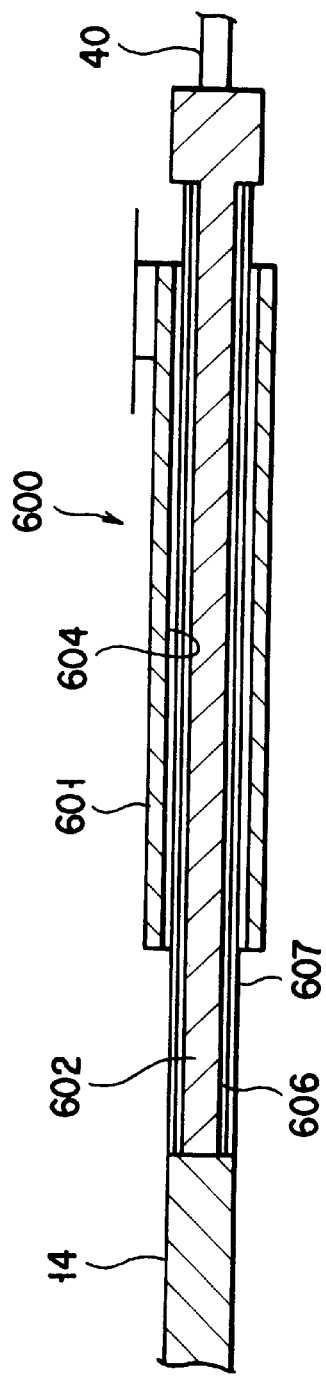
FIG. 31A is a longitudinal sectional view showing a schematic arrangement of an actuator according to the eleventh embodiment of the present invention.
Figure 31B:
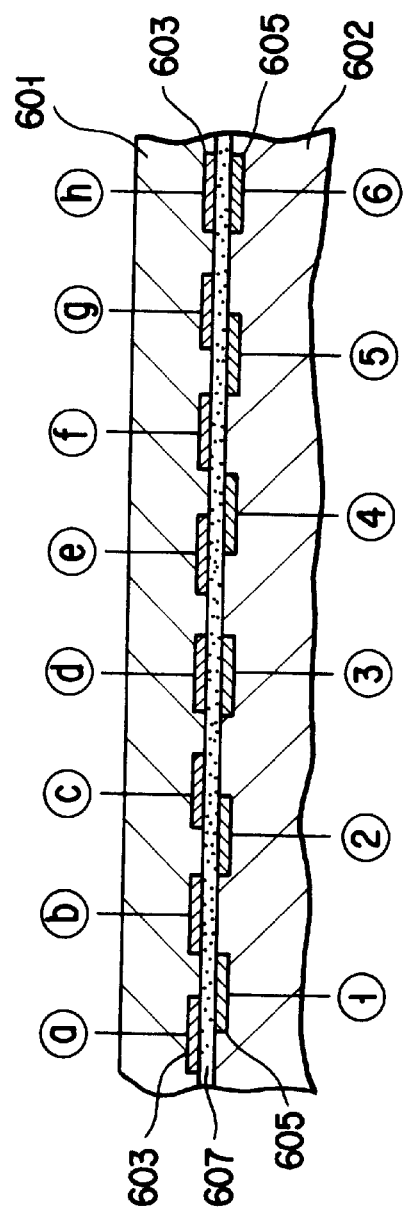
FIG. 31B is a longitudinal sectional view showing the arrangement of electrodes.

FIGS. 31A and 31B show the eleventh embodiment of the present invention. In the eleventh embodiment, an actuator 600 of an electrostatic driving scheme is used in place of the first to third artificial rubber muscles 121, 122, and 123 in the first embodiment.

This actuator 600 has a cylindrical stator 601. A movable element 602 is mounted in the stator 601 to be movable in the same direction of an angle wire 14.

In addition, as shown in FIG. 31B, an electrode layer 604 on which a plurality of electrodes 603 are arranged along the moving direction of the movable element 602 is formed on the inner surface of the stator 601.

Furthermore, an electrode layer 606 is formed on the outer surface of the movable element 602. A plurality of electrodes 605 are arranged on the electrode layer 606 along the direction in which the electrodes 603 on the stator 601 side are arranged. An insulating layer (resin layer) 607 is also formed on the outer surface of the electrode layer 606.

Note that one end portion of the movable element 602 is connected to the angle wire 14, while the other end is connected to a cable 40. One end portion of the stator 601 is fixed in an insertion portion 3. The stator 601 is electrically connected to a cable (not shown) electrically connected to the electrodes 603.

According to the above-described arrangement, in a bending operation of a bending portion 2, the movable element 602 of the actuator 600 is moved by an electrostatic driving force, and the angle wire 14 is moved in the axial direction upon movement of the movable element 602.

When the actuator 600 is driven, the patterns of voltage application to the electrodes 603 of the stator 601 and to the electrodes 605 of the movable element 602 are sequentially changed. Upon this change in voltage application pattern, the movable element 602 is linearly moved in the lateral direction.

The following Tables 1 and 2 show examples of changes in voltage application pattern with respect to the electrodes 603 of the stator 601 and the electrodes 605 of the movable element 602 during a driving period of the actuator 600. Assume, in this case, that the electrodes 603 of the stator 601 are sequentially denoted by reference symbols ⓐ to ⓗ, from left to right, as shown in FIG. 31B, and that the electrodes 605 of the movable element 602 are sequentially denoted by reference numerals ① to ⑥, from left to right, as shown in FIG. 31B. Tables 1 and 2 respectively show the patterns of voltage application (polarities of applied voltages) to the electrodes 603 respectively represented by ⓐ to ⓗ, and to the electrodes 605 respectively represented by ① to ⑥.

TABLE 1

| ⓐ | ⓑ | ⓒ | ⓓ | ⓔ | ⓕ | ⓖ | ⓗ |
|---|---|---|---|---|---|---|---|
| − | + | + | − | − | + | + | − |

| ① | ② | ③ | ④ | ⑤ | ⑥ |
|---|---|---|---|---|---|
| + | + | − | + | + | − |

According to Table 1, the electrodes ⓐ and ①, and the electrodes ⓔ and ④ are attracted to each other due to electrostatic attraction so that the movable element 602 is moved to the left in FIG. 31B. At this time, the repulsive forces between the electrodes ⓒ and ②, and the electrodes ⓖ and ⑤ also contribute to the moving operation of the movable element 602.

TABLE 2

| ⓐ | ⓑ | ⓒ | ⓓ | ⓔ | ⓕ | ⓖ | ⓗ |
|---|---|---|---|---|---|---|---|
| + | + | − | − | + | + | − | − |

| ① | ② | ③ | ④ | ⑤ | ⑥ |
|---|---|---|---|---|---|
| + | + | − | + | + | − |

According to Table 2, the electrodes ⓒ and ②, and the electrodes ⓖ and ⑤ are attracted to each other due to electrostatic attraction so that the moving element 602 is moved to the right in FIG. 31B. At this time, the repulsive forces between the electrodes ⓐ and ①, and the electrodes ⓔ and ④ also contribute the moving operation of the movable element 602.

FIGS. 32 and 33 show the twelfth embodiment of the present invention. The twelfth embodiment is obtained by changing the arrangement of the actuator 600 of the electrostatic driving scheme in the eleventh embodiment.

More specifically, an actuator 701 of an electrostatic driving scheme in this embodiment has a cylindrical stator 702. Three electrode layers 703a, 703b, and 703c of the same size are formed on the outer surface of the stator 702. A plurality of electrodes 603 are arranged on these electrode layers 703a, 703b, and 703c along the axial direction of the stator 702 in the same manner as in the eleventh embodiment.

In addition, movable elements 704a, 704b, and 704c are respectively arranged on the outer surfaces of the electrodes 703a, 703b, and 703c. An electrode layer 606 is formed on the inner surfaces of the movable elements 704a, 704b, and 704c. A plurality of electrodes 605 are arranged on the electrode layer 606 along the direction in which the electrodes 603 on the stator 702 sides are arranged, in the same manner as in the eleventh embodiment.

One end of each of the movable elements 704a, 704b, and 704c is connected to a corresponding one of angle wires 14, 16, and 18. The other end of each of the movable elements 704a, 704b, and 704c is connected to a corresponding one of cables 40, 42, and 44. The outer surfaces of the movable elements 704a, 704b, and 704c are covered with an outer tube 705.

In addition, as shown in FIG. 33, control sections 706a, 706b, and 706c for voltage application are respectively connected to the movable elements 704a, 704b, and 704c. These control sections 706a, 706b, and 706c are connected to a central control section 707 for synchronously controlling voltage application to the three movable elements 704a, 704b, and 704c. An operation portion 708 such as a joystick and a power source section 709 are connected to the central control section 707.

In a bending operation of a bending portion 2, the movable elements 704a, 704b, and 704c of the actuator 701 are axially moved by electrostatic driving forces, and the angle wires 14, 16, and 18 are moved in the axial direction upon movement of the movable elements 704a, 704b, and 704c.

During a driving period of the actuator 701, the patterns of voltage application to the electrodes 603 of the stator 702 and to the electrodes 605 of the respective movable elements 704a, 704b, and 704c are sequentially changed, and the movable elements 704a, 704b, and 704c are linearly moved in the lateral direction with changes in voltage application pattern.

FIG. 34 shows the thirteenth embodiment of the present invention. In this embodiment, the present invention is applied to the bending mechanism of a catheter 801 which is inserted into a patient, e.g., a pancreatic duct proper J through the duodenal papilla, through a tool insertion channel 824 formed in a large-diameter insertion portion 822 of a lateraloscope 821.

An insertion portion 802 of this catheter 801 includes a flexible tube portion 805 and a bending portion 804 coupled to the distal end side of the flexible tube portion 805. A plurality of joint pieces are arranged in the bending portion 804 along the axial direction of the insertion portion 802. Referring to FIG. 34, reference numeral 803 denotes the channel of the catheter 801; and 823, the distal end portion of the lateraloscope 821.

Three angle wires 812 for bending the bending portion 804 are arranged in the insertion portion 802 to extend over a predetermined length by which the insertion portion 802 is inserted into the pancreatic duct proper J. Three angle wires 812 are arranged at three positions in the insertion portion 802 at almost equal intervals in the circumferential direction. Note that only one angle wire 812 is shown in FIG. 34, but other angle wires 812 are omitted.

The distal end portion of this angle wire 812 is fixed to the distal end of the bending portion 804. In addition, the proximal portion of the angle wire 812 is connected to an SMA wire (actuator) 811 through a connecting member 825.

The proximal end portion of this SMA wire 811 is connected/fixed to the distal end portion of a lead wire 814 for an energization/heating operation through a caulking portion 813. The caulking portion 813 fixes the flexible tube portion 805.

The angle wires 812 are arranged in an exposed portion, of the insertion portion 802 of the catheter 801, which can be brought into contact with the wall of a body cavity, i.e., a portion of the catheter 801 which extends outward from the channel 824 of the lateraloscope 821 when the catheter 801 is inserted into a body cavity through the channel 824 of the lateraloscope 821, as shown in FIG. 34. The SMA wires 811 are arranged in a non-exposed portion of the insertion portion 802 of the catheter 801, i.e., a portion of the catheter 801 which does not extend outward from the channel 824 of the lateraloscope 821.

In addition, a stopper 826 (FIG. 40) is formed on an end portion of the catheter 801 on the manual operation side to limit the maximum insertion amount of the catheter 801 when the catheter 801 is inserted into a body cavity through the channel 824 of the lateraloscope 821. For example, this stopper 826 is constituted by a projection having a size D larger than the inner sized of the channel 824 of the lateraloscope 821.

If the catheter 801 is inserted into a body cavity through the channel 824 of the lateraloscope 821, the insertion of the catheter 801 is inhibited when the stopper is brought into contact with the edge portion of the opening of the channel 824 of the lateraloscope 821. In this state, the distal end of each SMA wire 811 of the catheter 801 is held inside the channel 824 of the lateraloscope 821.

In a bending operation of the bending portion 804 of the catheter 801 having the above-described arrangement, the SMA wire 811 is energized/heated by an energizing/heating unit (not shown) on the manual operation side through the lead wire 814. With this energizing/heating operation, the SMA wire 811 contracts.

Since the proximal end of the SMA wire 811 is fixed by the caulking portion 813, the angle wire 812 connected to the distal end of the SMA wire 811 is pulled backward. With this operation, since a pulling force acts on the folded portion of the angle wire 812, the bending portion 804 is bent.

In the apparatus having the above-described arrangement, the distal end of each SMA wire 811 of the catheter 801 is held inside the channel 824 of the lateraloscope 821 during a bending operation of the bending portion 804 of the catheter 801. This prevents conduction of heat generated by each SMA wire 811 during a bending operation of the bending portion 804 to the mucus on the wall of a body cavity, thus preventing the mucus from being damaged by heat.

FIGS. 35 to 37C show the fourteenth embodiment of the present invention. FIG. 35 shows a schematic arrangement of the distal end portion of a catheter 901. An insertion portion 902 of the catheter 901 is constituted by a flexible tube 903. A very narrow endoscope and various types of tools can be inserted into a channel 903a constituted by a central hole formed in the tube 903. In addition, injection of a contrast media/medicine, sucking of body fluids, and the like can be performed through the channel 903a.

As shown in FIGS. 36 and 37A, three pairs of wire insertion holes 904, each having a diameter smaller than that of the channel 903a, are formed in a tube wall 903b of the tube 903 in correspondence with the three bending directions of the catheter 901. The catheter 901 is constituted by a multi-lumen tube having the channel 903a and the six wire insertion holes 904, as shown in FIGS. 37A to 37C.

The outer surface of the tube 903 is covered with a covering tube 905 except for a distal end portion having a predetermined length. A bending portion 906 of the catheter 901 is constituted by this distal end portion of the tube 903 which is not covered with the covering tube 905.

Six SMA wires 907 are respectively inserted into the wire insertion holes 904 of the portion., of the tube 903, which is covered with the covering tube 905, whereas angle wires 908 which are lower in electric resistance than the SMA wires 907 are respectively inserted into the wire insertion holes 904 of the bending portion 906 which is not covered with the covering tube 905. Each angle wire 908 is constituted by one wire folded at a central portion. The two straight portions extending from this folded portion of each angle wire 908 are respectively inserted into the two wire insertion holes 904 arranged at one of the bending directions.

The distal end portions of the SMA wires 907 are respectively connected to the two end portions of each angle wire 908 through a pair of connecting portions 909. In this case, although spot welding or caulking may be performed to connect the angle wires 908 to the SMA wires 907 at the connecting portions 909, respectively, the outer size of each connecting portion 909 is set to be smaller than the inner size of each wire insertion hole 904 so as to allow the wire connecting portions 909 to slidably move along the wire insertion holes 904.

The proximal end portion of each SMA wire 907 is connected to the distal end portion of a corresponding lead wire 910 having an electric resistance lower than that of each SMA wire 907 through a caulking portion 911. The outer dimension of this caulking portion 911 is set to be larger than the inner dimension of the wire insertion hole 904 to be fixed therein.

An operation of the apparatus having the above-described arrangement will be described next. In a bending operation of the bending portion 906 of the catheter 901, each SMA wire 907 corresponding to a desired bending direction is energized/heated by an energizing/heating unit (not shown) on the manual operation side through the lead wire 910 and the angle wire 908. With this energizing/heating operation, the SMA wire 907 contracts.

Since the proximal end of the SMA wire 907 is fixed by the caulking portion 911, the angle wire 908 connected to the distal end of the SMA wire 907 is pulled backward upon contraction of the SMA wire 907. With this operation, since a pulling force acts on a folded portion of the angle wire 908, the bending portion 906 is bent.

In this case, since the bending portion 906 is not covered with the covering tube 905, its flexibility is higher than that of the portion which is covered with the covering tube 905. For this reason, deformation (bending) of the catheter 901 due to contraction of each SMA wire 907 is limited to the bending portion 906. That is, bending of the portion covered with the covering tube 905 is prevented.

In addition, in a bending operation of the catheter 901, each SMA wire 907 arranged in the tube wall 903b of the portion of the tube 903 which is covered with the covering tube 905 and corresponding to a desired bending direction is energized/heated, and the displacement of the SMA wire 907, caused by the energizing/heating operation, is transferred to the angle wire 908 arranged in the exposed portion of the tube wall 903b, thus bending the bending portion 906 of the catheter 901. This prevents heat from the SMA wire 907 which is heated to the highest temperature by the energizing/heating operation from being transferred outside.

Since there is no possibility that heat from each SMA wire 907 is transferred to the outer surface of the tube wall 903b of the bending portion 906 of the catheter 901, the outer surface of the bending portion 906 can be prevented from being heated to a high temperature, unlike the prior art. Therefore, when the catheter 901 is inserted into a body cavity of a patient, overheating of the inner wall of the body cavity can be reliably prevented, which is caused, as in the prior art, when the heated outer surface of the bending portion 906 is brought into contact with the inner wall of the body cavity.

Furthermore, since each angle wire 908 arranged in the bending portion 906 on the distal end side of the catheter 901, which is brought into contact with the inner wall of a body cavity, has an electric resistance much lower than that of each SMA wire 907, there is no possibility that the outer surface of the bending portion 906 is heated to a high temperature upon generation of heat from each angle wire 908, thus preventing overheating of the inner wall of the cavity.

Figure 38:
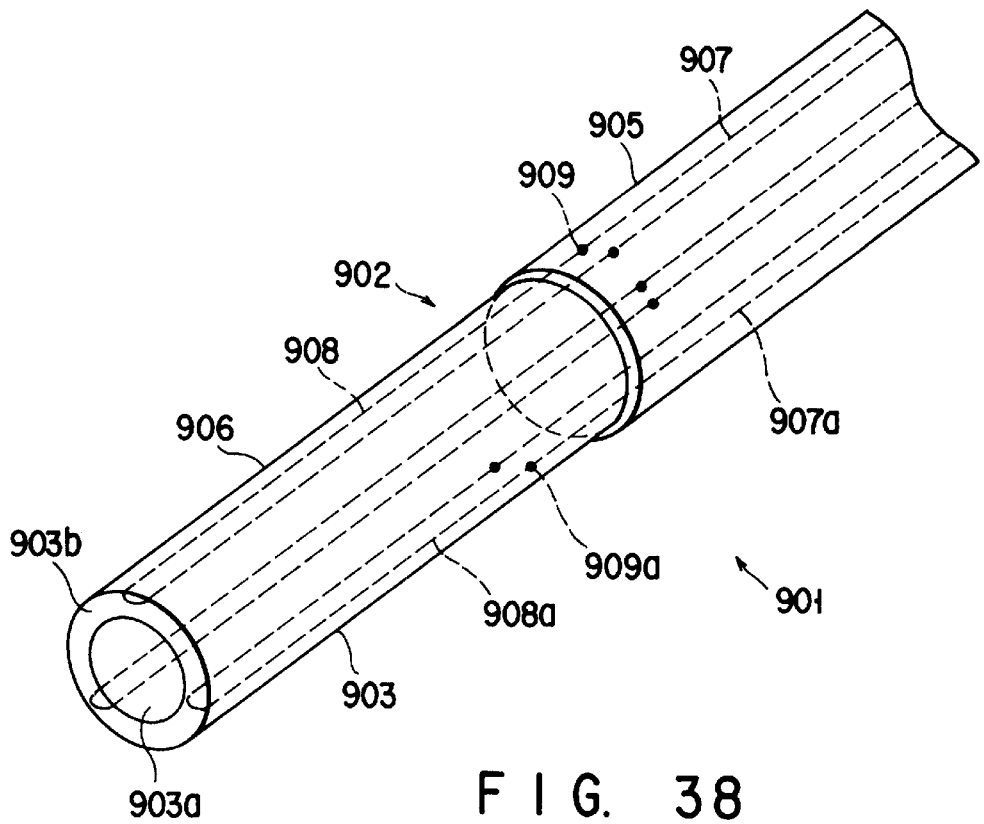
FIG. 38 is a perspective view showing a schematic arrangement of a main portion of the fifteenth embodiment of the present invention.

FIG. 38 shows the fifteenth embodiment of the present invention. This embodiment is the same as the fourteenth embodiment except that the distal end portions of SMA wires 907a arranged in a catheter 901 and corresponding to one of the three bending directions extend into a bending portion 906, and connecting portions 909a between the extending distal end portions of the SMA wires 907a and angle wires 908a are arranged in the bending portion 906.

In this case, since the remaining wires 907, which do not extend into the bending portion 906, are also arranged in a tube wall 903b of a portion of a tube 903 which is covered with a covering tube 905, the outer surface of the bending portion 906 can be prevented, unlike in the prior art, from being heated to a high temperature during a bending operation of the catheter 901, thus preventing overheating of the inner wall of a body cavity.

Figure 39:
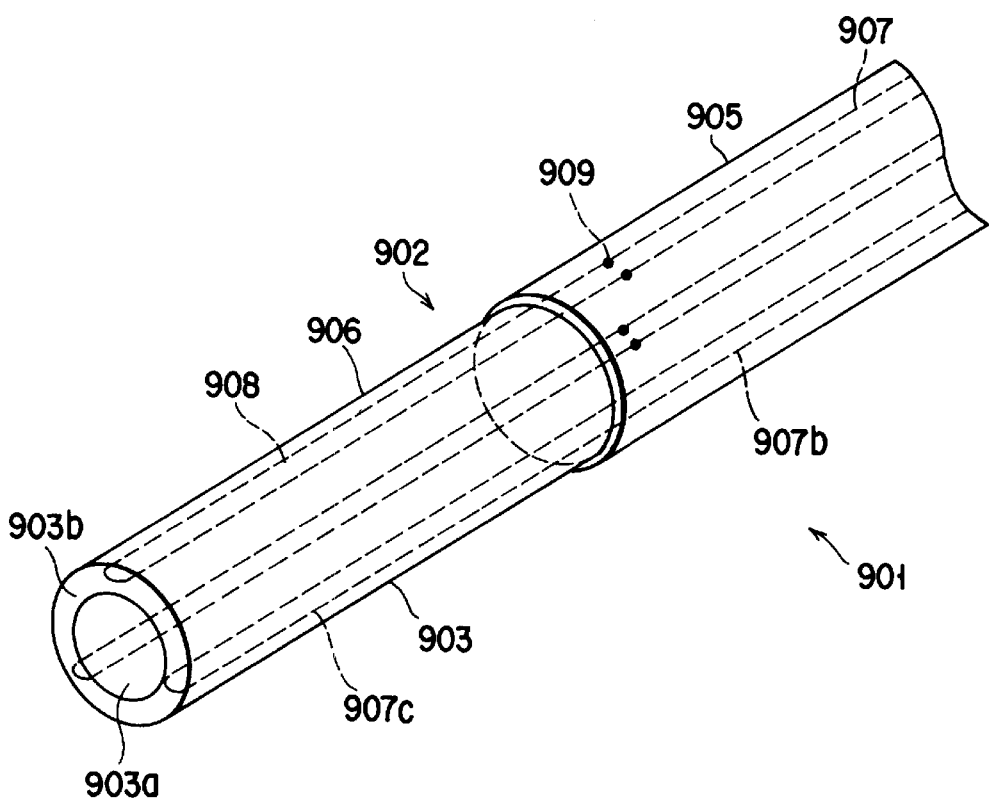
FIG. 39 is a perspective view showing a schematic arrangement of a main portion of the sixteenth embodiment of the present invention.

FIG. 39 shows the sixteenth embodiment of the present invention. This embodiment is the same as the fourteenth embodiment except that the distal end portions of SMA wires 907b arranged in a catheter 901 and corresponding to one of the three bending directions extend to the distal end side of a bending portion 906, and extending distal end portions 907c of the SMA wires 907b serve as angle wires.

In this case, since the remaining wires 907, which do not extend into the bending portion 906, are also arranged in a tube wall 903b of a portion of a tube 903 which is covered with a covering tube 905, the outer surface of the bending portion 906 can be prevented, unlike in the prior art, from being heated to a high temperature during a bending operation of the catheter 901, thus preventing overheating of the inner wall of a body cavity.

The present invention is not limited to the above-described embodiments. For example, it is apparent that the present invention can be applied to a bending mechanism for bending tools other than an endoscope and a catheter.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An endoscope apparatus comprising:
   an endoscope having a distal end, a port at the distal end, and a channel extending through said endoscope to the distal end and communicating with the port; and
   a bending insertion instrument extensible through the channel and through the port, the bending insertion instrument comprising:
   angle wires provided in a distal end side of the bending insertion instrument, and
   shape memory alloy wires connected to proximal end portions of the angle wires, and
   wherein the bending insertion instrument is inserted through the channel of the endoscope such that a portion of the bending insertion instruments, which is located on the distal end side of the bending insertion instrument and which includes the angle wires therein, is projected through the port.

2. An endoscope apparatus according to claim 1, wherein the endoscope apparatus further comprises:
   a control unit for controlling exposure of the bending insertion instrument outside of said endoscope through the channel and the port.

3. An endoscope apparatus according to claim 2, wherein said control unit includes, at a proximal portion of the bending insertion instrument inserted into the channel of the endoscope, a stopper for controlling a maximum insertion length of the bending insertion instrument.

4. The endoscope apparatus according to claim 1, wherein the bending insertion instrument has a channel for allowing an observing device to be inserted therethrough.

5. The endoscope apparatus according to claim 1, wherein the bending insertion instrument has a channel for allowing an operating device to be inserted therethrough.

6. The endoscope apparatus according to claim 1, wherein the bending insertion instrument has a channel serving as a passage for use in supplying and sucking fluid.

7. The endoscope apparatus according to claim 1, wherein the bending insertion instrument comprises a multi-lumen tube having a plurality of lumens, the angle wires and the shape memory alloy wires are inserted through the lumens, and connection portions of the angle wires and shape memory alloy wires are slidable within the lumens.

8. An endoscope apparatus according to claim 1, wherein said shape memory alloy wires do not extend into a portion of said distal end side of the bending insertion instrument which projects through the port.

9. An endoscope apparatus comprising:
  an endoscope having a distal end, a port at the distal end, and a channel extending through said endoscope to the distal end and communicating with the port; and
  a bending insertion instrument extensible through the channel and through the port, the bending insertion instrument comprising:
    angle wires provided in a distal end side of the bending insertion instrument, and
    shape memory alloy wires connected to proximal end portions of the angle wires, and
    wherein the bending insertion instrument is inserted through the channel of the endoscope such that (i) a portion of the bending insertion instrument, which includes the shape memory alloy wires, is located in the channel of the endoscope, and (ii) a portion of the bending insertion instrument, which includes the angle wires therein, is located on the distal end side of the bending insertion instrument and is projected through the port.

10. An endoscope apparatus according to claim 9, wherein the endoscope apparatus further comprises:
  a control unit for controlling exposure of the bending insertion instrument outside of said endoscope through the channel and the port.

11. An endoscope apparatus according to claim 10, wherein said control unit includes, at a proximal end portion of the bending insertion instrument inserted into the channel of the endoscope, a stopper for controlling a maximum insertion length of the bending insertion instrument.

12. An endoscope apparatus according to claim 9, wherein said shape memory alloy wires are directly connected to proximal ends of respective angle wires.

13. An endoscope apparatus according to claim 9, wherein said shape memory alloy wires do not extend into a portion of said distal end side of the bending insertion instrument which projects through the port.

14. An endoscope apparatus comprising:
  an endoscope having a channel communicating with an outside of the endoscope; and
  a bending insertion instrument capable of being exposed to an outside of the endoscope through the channel of the endoscope, the bending insertion instrument including:
    angle wires provided at a distal end portion of the bending insertion instrument, and
    shape memory alloy wires electrically connected to proximal end portions of the angle wires,
    and wherein an electrical resistance of the angle wires is lower than an electrical resistance of the shape memory alloy wires.

15. An endoscope apparatus according to claim 14, wherein the angle wires have distal end portions which are bent back, and proximal end portions which are electrically connected to the shape memory alloy wires.

16. An endoscope apparatus according to claim 14, wherein the distal end portion of the bending insertion instrument at which the angle wires are arranged is more flexible than a proximal end portion of the bending insertion instrument so as to form a bending portion at said distal end portion.

17. An endoscope apparatus according to claim 16, wherein:
  the bending insertion instrument comprises a covering tube provided at the proximal end portion of the bending insertion instrument; and
  a portion of the bending insertion instrument at which the covering tube is not provided is formed as the bending portion of the bending insertion instrument.

18. An endoscope apparatus according to claim 16, wherein the shape memory alloy wires are provided at a backward side of the bending portion of the bending insertion instrument.

19. An endoscope apparatus according to claim 14, wherein proximal end portions of the shape memory alloy wires are electrically connected to lead wires having a lower electrical resistance than that of the shape memory alloy wires.

20. The endoscope apparatus according to claim 19, wherein the proximal end portions of the shape memory alloy wires are connected to the lead wires by caulking members, and the caulking members are fixed within the bending insertion instrument.

21. The endoscope apparatus according to claim 19, wherein the bending insertion instrument comprises a multi-lumen tube having a plurality of lumens, the shape memory alloy wires and the lead wires are inserted through the lumens, and caulking members are provided to connect the angle wires and the shape memory alloy wires, the caulking members having diameters which are greater than inside diameters of the lumens.

22. An endoscope apparatus according to claim 1, wherein said shape memory alloy wires are directly connected to proximal ends of respective angle wires.

23. A bending operation apparatus for operating a bending insertion instrument which has an insertion section which is insertable into one of a digestive organ of a human body, a body cavity, an industrial tube, and a work space, and a bending portion arranged at a distal end portion of the insertion section and being capable of bending,
  the bending operation apparatus further comprising:
    angle wires provided in the bending portion at the distal end portion of the insertion section of the bending insertion instrument, and
    shape memory alloy wires electrically connected to proximal end portions of the angle wires, the angle wires having a lower electrical resistance than an electrical resistance of the shape memory alloy wires.

24. A bending operation apparatus according to claim 23, wherein the angle wires have distal end portions which are bent back, and proximal end portions which are electrically connected to the shape memory alloy wires.

25. A bending operation apparatus according to claim 23, wherein the bending portion at the distal end portion of the insertion section of the bending insertion instrument, at which the angle wires are arranged, is more flexible than a proximal end portion of the bending insertion instrument.

26. A bending operation apparatus according to claim 25, wherein:
  the bending insertion instrument comprises a covering tube provided at the proximal end portion of the bending insertion instrument; and
  a portion of the bending insertion instrument at which the covering tube is not provided is the bending portion of the insertion section of the bending insertion instrument.

27. A bending operation apparatus according to claim 26, further comprising:
  a shape memory alloy wire which extends through said insertion section and which further extends into the bending portion of the distal end portion of the insertion section of the bending insertion instrument.

28. A bending operation apparatus according to claim 25, wherein the shape memory alloy wires are provided at a backward side of the bending portion of the insertion section of the bending insertion instrument.

29. A bending operation apparatus according to claim 23, wherein the bending insertion instrument comprises a covering tube at a portion at which the shape memory alloy wires are provided.

30. A bending operation apparatus according to claim 23, wherein proximal end portions of the shape memory alloy wires are electrically connected to lead wires having a lower electrical resistance than that of the shape memory alloy wires.

31. A bending operation apparatus according to claim 23, wherein the angle wires have distal end portions which are fixed in the bending insertion instrument.

32. A bending operation apparatus according to claim 23, wherein:

the bending insertion instrument has a plurality of lumens each of which is provided with one of the angle wires, one of the shape memory alloy wires, and one of the lead wires; and the shape memory alloy wires and the lead wires are connected to each other at a connecting point thereof by means of a caulking member having an outer diameter larger than an inner diameter of the lumens, said caulking member is fixed to the lumens.

33. A bending operation apparatus according to claim 23, wherein a distal end portion of one of said shape memory alloy wires is located in the bending portion.

34. A bending operation apparatus according to claim 23, wherein said shape memory alloy wires are directly connected to proximal ends of respective angle wires.

35. A bending operation apparatus according to claim 23, wherein said shape memory alloy wires do not extend into said bending portion at the distal end portion of the insertion section of the bending insertion instrument.

* * * * *